US011266309B2

(12) United States Patent
Katz et al.

(10) Patent No.: US 11,266,309 B2
(45) Date of Patent: Mar. 8, 2022

(54) EYE EXAMINATION KIOSK SYSTEM AND METHOD FOR REMOTE EYE EXAMINATION

(71) Applicant: GlobeChek Intellectual Holdings, LLC, Kent Country, DE (US)

(72) Inventors: Adam M. Katz, Vero Beach, FL (US); William J. Mallon, Vero Beach, FL (US); David Gary Eldridge, Brentwood, CA (US)

(73) Assignee: Globechek Intellectual Holdings, LLC, Kent Country, DE (US)

( * ) Notice: Subject to any disclaimer, the term of this patent is extended or adjusted under 35 U.S.C. 154(b) by 0 days.

(21) Appl. No.: 16/334,005

(22) PCT Filed: Sep. 17, 2017

(86) PCT No.: PCT/US2017/051946
§ 371 (c)(1),
(2) Date: Mar. 16, 2019

(87) PCT Pub. No.: WO2018/053377
PCT Pub. Date: Mar. 22, 2018

(65) Prior Publication Data
US 2019/0290126 A1    Sep. 26, 2019
US 2021/0275021 A9    Sep. 9, 2021

Related U.S. Application Data

(63) Continuation-in-part of application No. PCT/US2016/068410, filed on Dec. 22, 2016, and a
(Continued)

(51) Int. Cl.
*A61B 3/10* (2006.01)
*A61B 3/18* (2006.01)
(Continued)

(52) U.S. Cl.
CPC .............. *A61B 3/18* (2013.01); *A61B 3/0025* (2013.01); *A61B 3/0083* (2013.01); *A61B 3/024* (2013.01);
(Continued)

(58) Field of Classification Search
CPC ......... A61B 3/18; A61B 5/1176; G06F 3/013; G06F 21/32
(Continued)

(56) References Cited

U.S. PATENT DOCUMENTS 4,237,796 A * 12/1980 Gordon .................... A61B 3/18
108/103
6,364,484 B2    4/2002 Yamada
(Continued)

FOREIGN PATENT DOCUMENTS

WO    WO2013188683    12/2013

OTHER PUBLICATIONS

Non-Final Office Action dated Aug. 7, 2017, U.S. Appl. No. 15/268,572.
(Continued)

*Primary Examiner* — Mahidere S Sahle
(74) *Attorney, Agent, or Firm* — Lowndes Law; Stephen C. Thomas

(57) ABSTRACT

The eye examination kiosk and method may comprise a structure for rotating and/or translating ophthalmologic examination devices such as an auto-refractor, an auto-keratometer, a corneal topographer, a fundus camera, an external photo camera, a perimeter, a lensmeter, a specular microscope, a retinal and external eye imager, an Optical Coherence Tomographer (OCT), or a non-contact tonometer into a position such that they may be used for examination of a patient. The kiosk outer shell may comprise an opening allowing the ophthalmologic examination equipment to per-
(Continued)

form eye examinations of a patient. Eye examination results are transmitted to a remote location where they are read by a physician, who transmits examination findings and recommendations for follow up treatment to the patient. The results may include the identity of qualified physicians who practice geographically near the patient, or who are qualified to treat a patient for a specific condition indication.

29 Claims, 31 Drawing Sheets

Related U.S. Application Data continuation-in-part of application No. 15/268,572, filed on Sep. 17, 2016, now abandoned.

(51) Int. Cl.
    *A61B 3/00*     (2006.01)
    *A61B 3/024*     (2006.01)
    *A61B 3/103*     (2006.01)
    *A61B 3/107*     (2006.01)
    *A61B 3/13*     (2006.01)
    *A61B 3/14*     (2006.01)
    *A61B 3/16*     (2006.01)

(52) U.S. Cl.
    CPC .............. *A61B 3/102* (2013.01); *A61B 3/103* (2013.01); *A61B 3/107* (2013.01); *A61B 3/13* (2013.01); *A61B 3/14* (2013.01); *A61B 3/165* (2013.01)

(58) Field of Classification Search
    USPC .................................................. 351/205–246
    See application file for complete search history.

(56) References Cited

U.S. PATENT DOCUMENTS

| | | | |
|---|---|---|---|
| 6,594,607 B2 | 7/2003 | Lavery | |
| 7,232,220 B2 | 6/2007 | Franz et al. | |
| 7,384,146 B2 | 6/2008 | Covannon et al. | |
| 7,520,611 B2 | 4/2009 | Franz et al. | |
| 7,614,747 B2 | 11/2009 | Foster | |
| D621,524 S | 8/2010 | Olson | |
| 8,182,091 B2 | 5/2012 | Foster | |
| D668,720 S | 10/2012 | Mascarelli | |
| 8,526,573 B2 | 9/2013 | Ferro, Jr. | |
| 8,740,386 B2 | 6/2014 | Foster | |
| 8,820,931 B2 | 9/2014 | Walsh et al. | |
| 2002/0003608 A1 | 1/2002 | Yamada | |
| 2008/0189173 A1 | 8/2008 | Baker et al. | |
| 2009/0128778 A1 | 5/2009 | Honda et al. | |
| 2009/0310084 A1 | 12/2009 | Foster | |
| 2012/0126072 A1 | 5/2012 | Pettersson | |
| 2012/0293642 A1* | 11/2012 | Berini | G06F 21/32 348/77 |
| 2013/0141694 A1 | 6/2013 | Seriani | |
| 2013/0293837 A1 | 11/2013 | Akiba | |
| 2013/0334851 A1 | 12/2013 | Hoell et al. | |
| 2013/0339043 A1* | 12/2013 | Bakar | A61B 3/185 705/2 |
| 2014/0129259 A1 | 5/2014 | Seriani | |
| 2014/0139805 A1 | 5/2014 | Carnevale | |
| 2015/0062878 A1 | 3/2015 | Danson | |
| 2016/0045108 A1 | 2/2016 | Wu | |
| 2016/0171596 A1 | 6/2016 | Angerbauer | |
| 2016/0262617 A1 | 9/2016 | Gerrans | |

OTHER PUBLICATIONS

Final Office Action dated Mar. 27, 2018, U.S. Appl. No. 15/268,572.
Non-Final Office Action dated Mar. 7, 2019, U.S. Appl. No. 15/268,572.
International Search Report and Written Opinion, PCT/US2017/051946 dated Jan. 18, 2018.
International Search Report and Written Opinion, PCT/US2016/068410 dated Mar. 16, 2017.

* cited by examiner

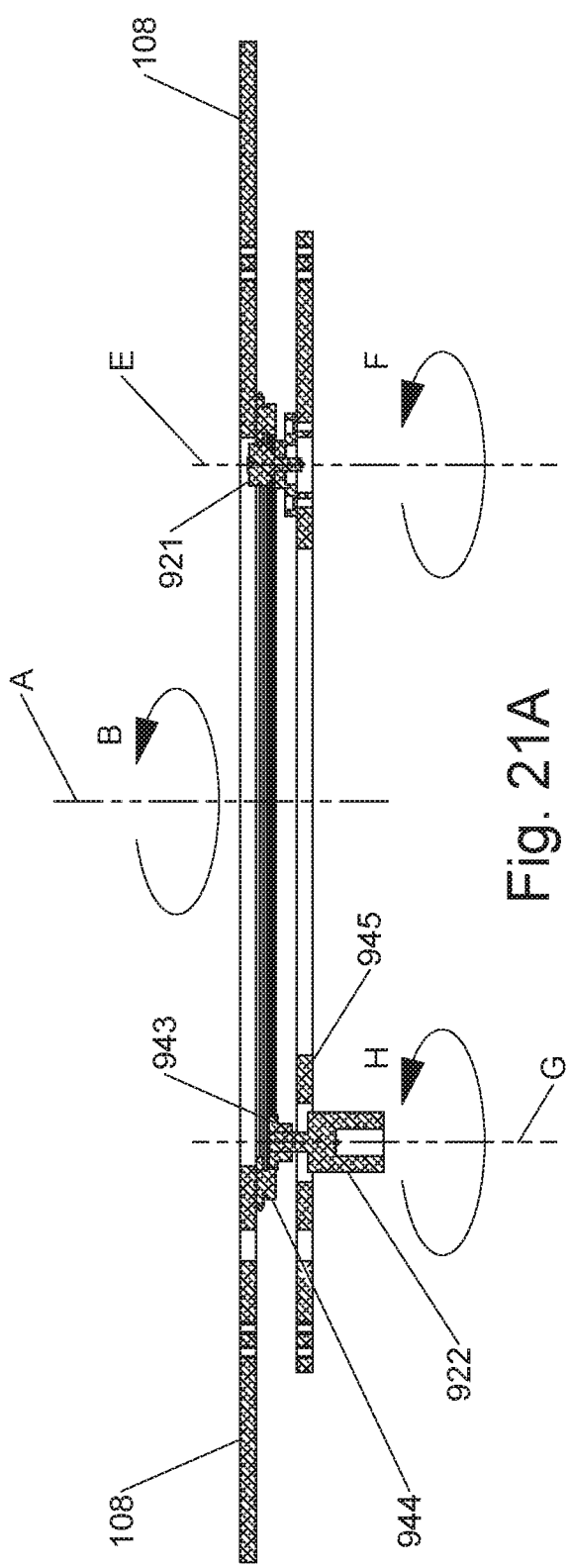
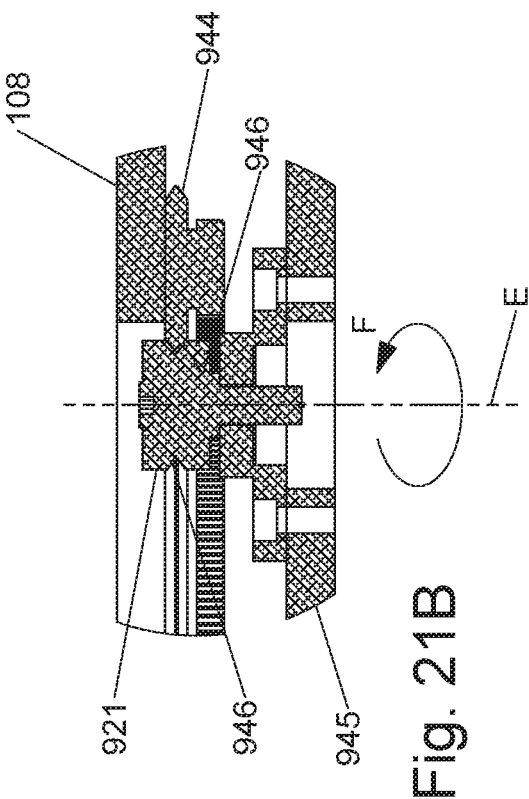

EYE EXAMINATION KIOSK SYSTEM AND METHOD FOR REMOTE EYE EXAMINATION

CROSS REFERENCE TO RELATED APPLICATIONS AND INCORPORATION BY REFERENCE

This international patent application, filed under the Patent Cooperation Treaty, claims benefit of priority to, and is a continuation in part of, international patent application number PCT/US16/68410 titled EYE EXAMINATION KIOSK, SYSTEM AND METHOD FOR REMOTE EYE EXAMINATION which was filed in the United States Receiving Office (USRO) on Dec. 22, 2016, which is herein incorporated by reference in its entirety and which claimed benefit of priority to U.S. non provisional patent application Ser. No. 15/268,572 for EYE EXAMINATION KIOSK, SYSTEM AND METHOD FOR REMOTE EYE EXAMINATION, filed in the United States Patent and Trademark Office on Sep. 17, 2016, which is hereby incorporated by reference in its entirety: this international patent application also claims benefit of priority to, and is a continuation in part of, U.S. non provisional patent application Ser. No. 15/268,572 for EYE EXAMINATION KIOSK, SYSTEM AND METHOD FOR REMOTE EYE EXAMINATION, filed in the United States Patent and Trademark Office on Sep. 17, 2016, which is hereby incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The field of the invention relates generally to systems and methods for providing screening eye examinations for patients. More specifically, the field of the invention relates to systems and methods for providing screening eye examinations wherein test results are taken at an examination site, transmitted to a remote site, and analyzed by a qualified person at the remote site, with examination results and recommendations for medical follow up being transmitted to the patient via a communication means.

2. Background Art

Eye examinations typically occur in an ophthalmologist's office. A patient generally follows a series of steps to secure an ophthalmologic examination, the steps typically comprising contacting the ophthalmologist's office, setting an appointment at a future time and date, traveling to the ophthalmologist's office, waiting for the ophthalmologist to become available, sitting for the ophthalmologic examination, holding a discourse with the ophthalmologist, holding a discourse with office staff which may include making arrangements for paying for the examination and setting of future appointments, and returning from the ophthalmologist's office. The time required to secure an ophthalmologic examination may range up to several hours depending upon such factors as the distance to the ophthalmologist's office, the ophthalmologist office workload, unforeseen interruptions or emergencies and the like. The total completion time, from setting of appointment until the examination is completed, can take weeks or longer.

What is needed in the art, therefore, is an apparatus and/or method adapted to increasing the convenience of securing an ophthalmologic screening examination by, for example, reducing the time required for examination, integrating the opportunity for ophthalmologic examination into the activities and routines of daily life, and providing quick and easy follow up for future ophthalmologic care and treatment.

BRIEF SUMMARY OF THE INVENTION

The present invention comprises an apparatus and method that have one or more of the following features and/or steps, which alone or in any combination may comprise patentable subject matter.

The present invention overcomes the shortcomings of the prior art in that it provides a method and apparatus for reducing the time required for eye examination, allowing for the integrating of ophthalmologic examination into the activities and routines of daily life, and providing quick and easy follow up for future ophthalmologic care and treatment.

In accordance with one embodiment of the present invention, the invention comprises an eye examination kiosk that may be placed in any area convenient to prospective patients. Such areas may include retail centers such as shopping malls; travel centers such as airports; schools; or any other building or facility. The eye examination kiosk may also be located on a mobile platform such as a motor vehicle or trailer such that it can be transported to any location convenient for prospective patients.

The eye examination kiosk may comprise an internal structure for attaching ophthalmologic examination devices. The internal structure may comprise a mechanical structure for attaching ophthalmologic examination devices and for rotating and/or translating the ophthalmologic examination devices into a position such that the ophthalmologic examination equipment may be used for ophthalmologic examination of a patient. The kiosk may also comprise an outer housing, shell, or cover, within which the internal structure and ophthalmologic examination equipment are contained. The kiosk may be able to be translated up or down along an axis by command of a controller such that patients of varying heights may be examined, including patients in a wheelchair, scooter, or other mobility device. The kiosk outer shell may provide one or more openings adapted to allow a user to access the ophthalmologic examination devices and for interacting with a kiosk management system by, for example, accessing a touch screen monitor or keyboard, and for viewing information displayed on a visual display that is a part of the kiosk management system. Eye examination results may be transmitted to a remote location where they may be stored and remotely read and interpreted by a qualified physician, who may transmit the examination findings to the patient, the patient's health care provider, or any other person or entity designated by the patient. The eye examination results may include recommendations for follow up treatment and recommendations as to the identity of qualified physicians who practice in a location that is geographically near the patient, or who are specially qualified to treat a patient for a specific condition or medical indication.

The ophthalmologic examination devices may be a computer controlled system that executes non-transitory computer executable instructions stored in a physical non-transitory computer readable media for carrying out the method steps of the invention. The computer, or controller, of the invention may be in communication with each of the actuators of the kiosk, the rotary table upon which the eye examination devices are mounted, and with external data networks for communicating eye examination results to at least one remote server for reading by a physician. Each of the functions of the ophthalmologic examination devices may be commanded by the controller executing non-transitory computer executable instructions stored in a physical non-transitory computer readable media.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating the preferred embodiments of the invention and are not to be construed as limiting the invention. In the drawings:

FIGS. 21A and 21B depict a side cross section view of a portion of the rotary drive assembly of an embodiment of the invention.

DETAILED DESCRIPTION OF THE INVENTION

Figure 1:
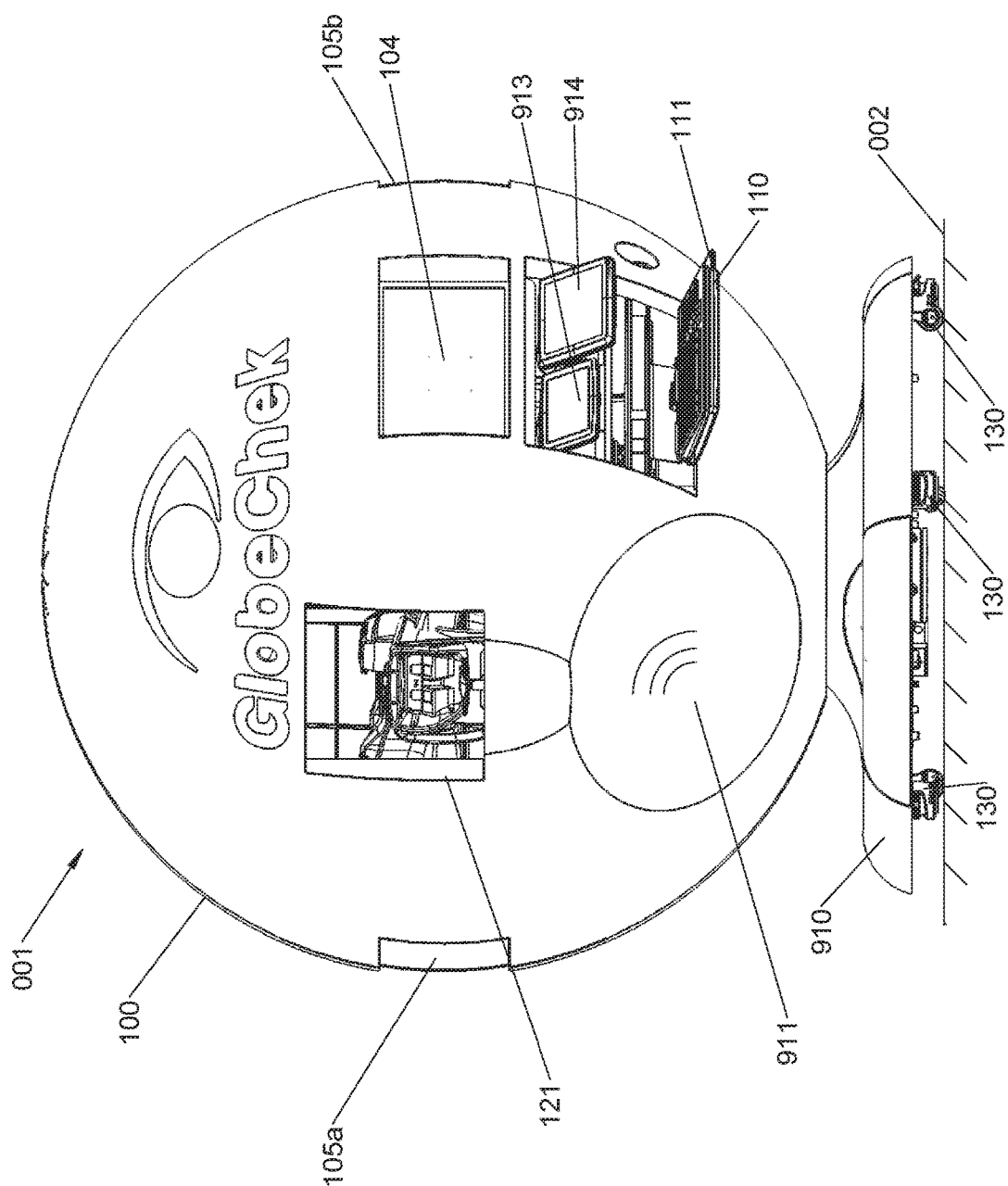
FIG. 1 depicts an exterior side view of an embodiment of the eye examination kiosk of the invention.

The following documentation provides a detailed description of the invention.

Although a detailed description as provided in the attachments contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention. Thus the scope of the invention should be determined by the appended claims and their legal equivalents, and not merely by the preferred examples or embodiments given.

As used herein, "memory", "medium", "media", "computer readable memory", "computer readable medium", "computer readable media", "storage media", "computer readable storage media" and "computer readable storage medium" shall include within their meanings only physical non-transitory computer readable hardware, and such terms shall specifically exclude signals per se, carrier waves, propagating signals and other transitory signals. Such physical non-transitory computer readable media may comprise hardware memory that comprises a physical structure for storing data which may include computer executable instructions or data.

As used herein, "controller" shall include within its meeting any electronic device or combination of electronic devices or other electronic elements which is or are capable of executing non-transitory computer readable instructions. Such devices or elements may include processors, microprocessors, microcontrollers, firmware controllers, field programmable gate arrays, programmable array logic devices, or any other devices or systems known in the art capable of performing the above functions. Such electronic devices or other electronic elements may comprise any number of actual physical hardware devices or emulators that need not be co-located; in other words, the execution of non-transitory computer readable instructions to carry out the steps of the invention, or to provide features of the invention may be distributed among one or more such actual physical hardware devices or emulated devices. The execution of non-transitory computer readable instructions may be used to carry out any of the steps of the invention, or provide any feature of the invention, that such instruction execution is capable of providing as is known in the art.

As used herein, "computer" and "server" shall include within their meanings any combination of electrical devices as is known in the art for inputting instructions to a controller and receiving information from a controller such as, for example, by means of a visual display such as a computer monitor. Include within the meaning of "computer" and "server" are controllers, input devices, transceivers for data connections and non-transitory computer readable media for the storage of computer executable instructions, all of which may be in communication with one another, such that the controller is able to read non-transitory computer readable and executable instructions, and to execute such instructions for the purposes of carrying out the objects, steps and functions of the invention.

As used herein, "eye examination device" and "ophthalmologic examination device" have the same meaning.

The eye examination kiosk of the invention may comprise a rotable table upon which is mounted one or more eye examination devices. The rotable table may be enclosed and rotable within a kiosk outer shell. The rotable table and outer shell may be translatable in a vertical direction, up or down, as may be desired by a user. Such translation allows the alignment of the eye examination devices with the eye of a user, and thus enables the kiosk to adapt its effective examination height to users of various heights. The kiosk may comprise legs that may rest upon a support surface such as a floor, or the legs may be supported by optional casters which provide a rolling engagement between the support surface and the eye examination kiosk, allowing the kiosk of the invention to be rolled into a desired location and orientation. The kiosk outer shell may take any desired shape such as, for example, a portion of a parallelepiped, which may be a portion of a rectangular parallelepiped, but which, in a preferred embodiment, may be defined as a sphere or a portion of a sphere. One such spherical embodiment, of many embodiments, is depicted in the figures. The eye examination devices may comprise any eye examination device, including but not limited to one or more of the following, in any combination: an auto-refractor, auto-keratometer, corneal topographer, fundus camera, external photo camera, perimeter, lensmeter, specular microscope, retinal and external eye imager, Optical Coherence Tomographer (OCT), and non-contact tonometer. While the figures of the drawings depict embodiments of the invention that comprise some of these instruments, in alternate embodiments of the invention any combination of these inventions, in any number, may be present. The examinations performed by the eye examination devices may occur in any order. The eye examination devices may be rotated into an examination position by rotation of the rotable table, which is in communication with a controller that controls the table rotation.

Referring now to FIG. 1, an exterior side view of eye examination kiosk 001 of the invention is depicted. Kiosk 001 may comprise a kiosk outer shell 100 and a leg cover 910 that may cover a plurality of legs comprising caster assemblies 130. While the kiosk may comprise any number of legs, a preferred number of legs for stability of the kiosk is five, and although caster assemblies 130 are optional, it is preferred that each leg comprise one caster 130. The optional caster assemblies 130 may comprise wheels, balls or other structures for providing a rolling engagement between the eye examination kiosk 001 and a surface 002 upon which it rests. The eye examination kiosk 011 may comprise a first display 105a, a second display 105b (not shown in FIG. 1, but shown in FIG. 2) and a third display 104 each of which may be electronic displays such as, for example liquid crystal displays (LCDs), light emitting diode (LED) displays, plasma displays, cathode ray tube (CRT) displays, or any other displays known in the art. Displays 105a and 105b are preferably electronic flat screen displays but may be any display, such as static, no-electronic signs. In the embodiments in which displays 104, 105*a* and 105*b* are electronic displays, they may each be in communication with a controller 700 (not shown in FIG. 1) that provides display information to the displays. The display information may be any information, for example, advertisements, patient queues, eye-related or other health related information, or more specifically may be advertisements for services or products related to eye health, eye care, eye examination, corrective lenses, or other eye-related products or services. Furthermore, displays 104, 105*a* and 105*b* may also be touch screen displays for use by a patient or other person to provide input to the controller. Each eye examination device may comprise a chin rest or a forehead rest, or both, usable to positively locate a patient's head in a desired location such that the patient's eye is located at a predefined plane of examination. As the eye examination devices are rotated into an examination position by command of the rotary table 108, as described further herein, the plane of examination of each device is presented to a patient in examination opening 121, which is an opening in outer shell 100, such that the patient may place their eye or eyes at the place of examination of the eye examination device and thus undergo eye examination. The plane of examination for an eye examination device is defined to be a plane that is located a predefined distance from an eye examination device as required for a specific eye examination device to perform a desired eye examination of a patient. Keyboard 111, mouse 112 and joystick 114 (not shown in FIG. 1) may reside on a keyboard shelf 110 for use by a user, which may be a patient or examination assistant. Keyboard 111, mouse 112, joystick 114 and other computer input and output devices, may be in communication with the controller 700 of the invention (not shown in FIG. 1) and may be used by a patient, examination assistant, or other person to provide input signals to the controller to command the controller to carry out the steps and functions of the invention. The eye examination kiosk 001 may further comprise electronic display 913 or 914, or both, each of which may be in communication with an eye examination device for controlling the device, viewing test results, viewing eye examination device status, or otherwise communicating with the eye examination device. Electronic display 913 or 914 may be touch screens. The eye examination kiosk outer shell 100 may further comprise a recess 911 for accommodating the legs or lower torso of a patient who may be bound to a wheelchair, scooter or other mobility device. Keyboard shelf 110, which may support keyboard 111, mouse 112, and joystick 114, may be attached to, or form a part of, outer shell element 100.

Figure 2:
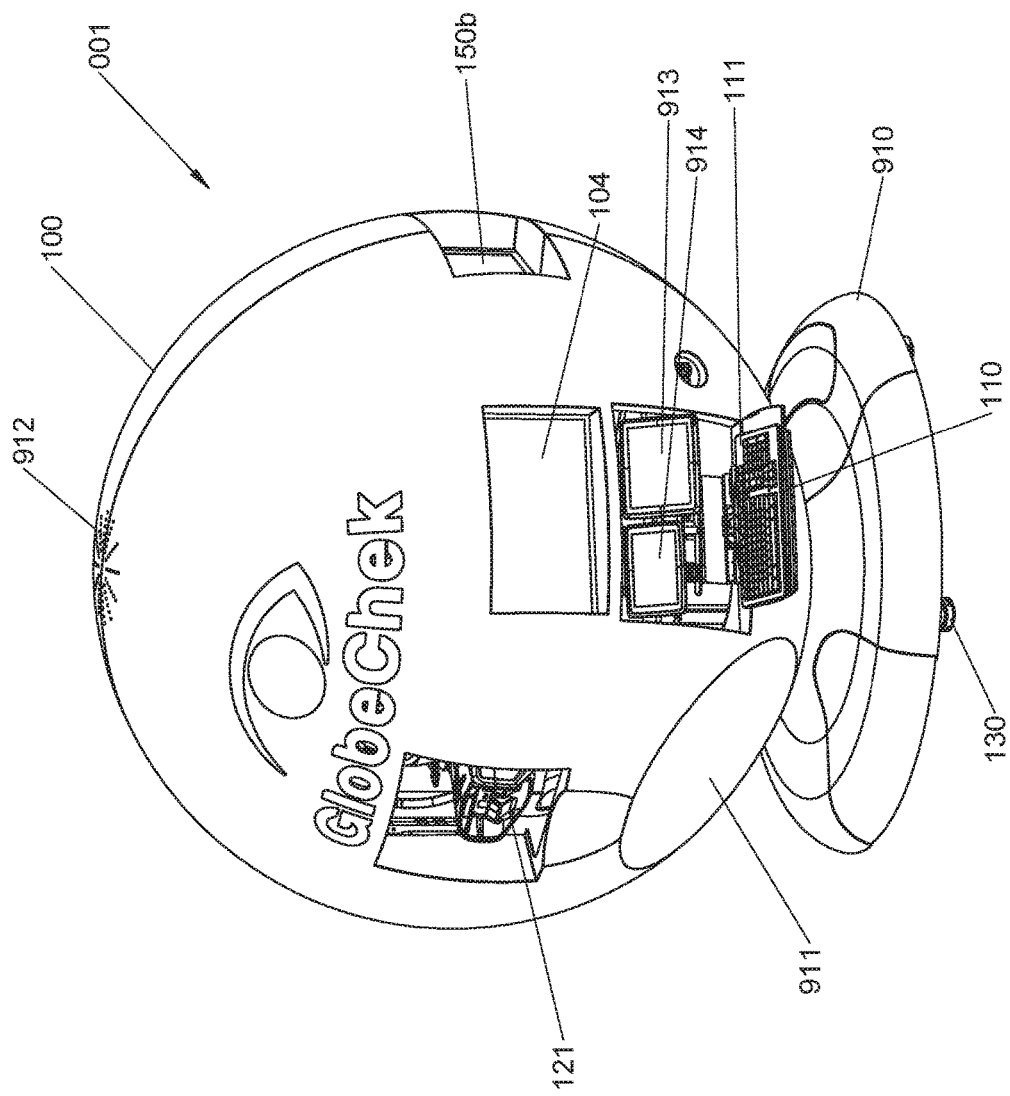
FIG. 2 depicts a top view of an perspective view of the eye examination kiosk of the invention.

Referring now to FIG. 2, a perspective view of an embodiment of eye examination kiosk 001 of the invention is depicted. Kiosk outer shell 100 may comprise a kiosk rear surface 103, which may be useful for locating the kiosk against a wall or other vertical flat surface when in operation or storage. Optional casters 130 are shown for reference. Displays 104 and 105*b*, keyboard 111, keyboard shelf 110, are also shown for reference. Recess 911, examination opening 121 leg cover 910, and displays 913 and 914 are shown for reference. Optional air vent 912 allows air to be pulled into or exhausted from within the outer shell 100 by an internal fan.

Figure 3:
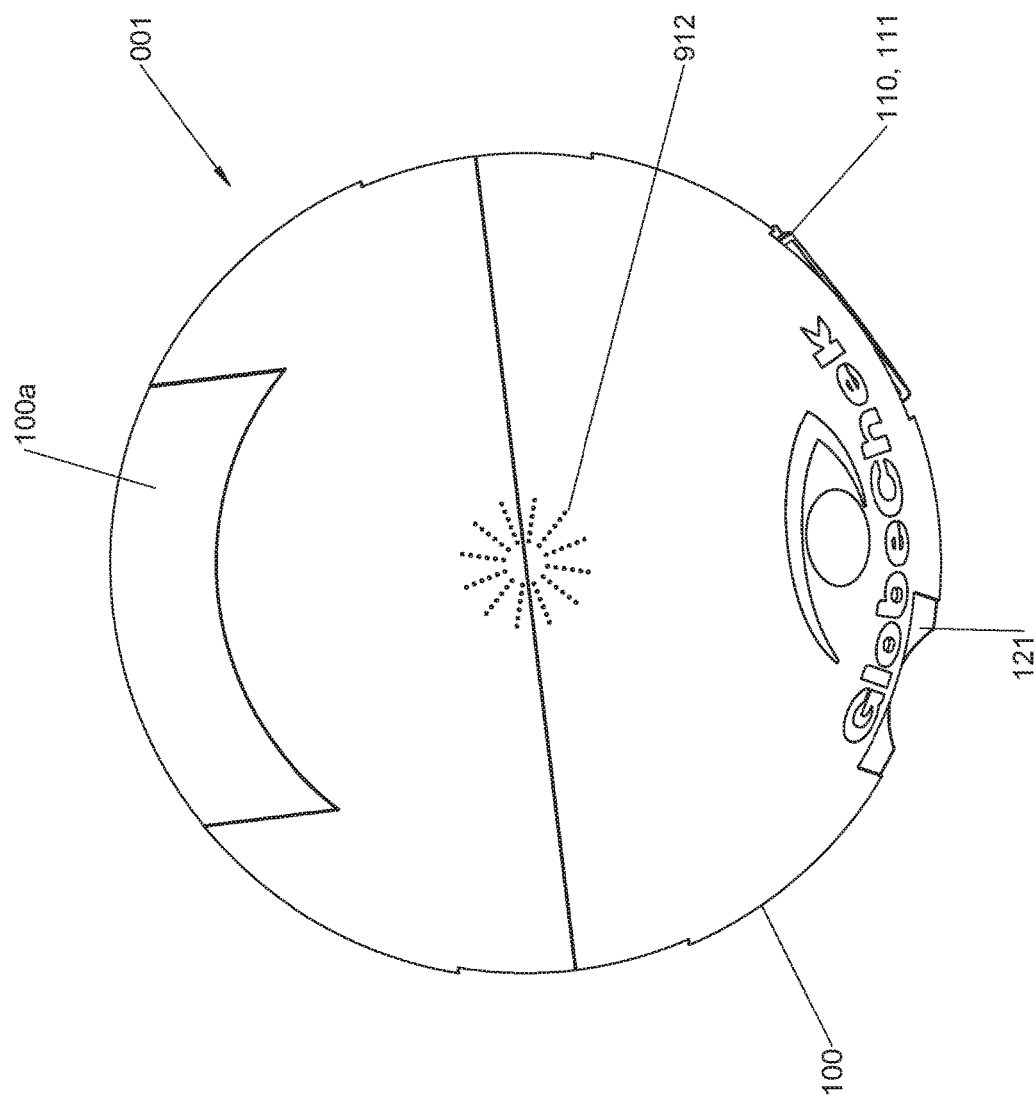
FIG. 3 depicts a top view of an embodiment of the eye examination kiosk of the invention.

Referring now to FIG. 3, a top orthogonal view of an embodiment of eye examination kiosk 001 is depicted. Air vent 912, outer shell 100, keyboard 111 and keyboard shelf 110, and examination opening 121 are depicted for reference. Outer shell may comprise a removable portion 100*a* to allow access for internal cleaning and maintenance of the eye examination kiosk 001.

Figure 4:
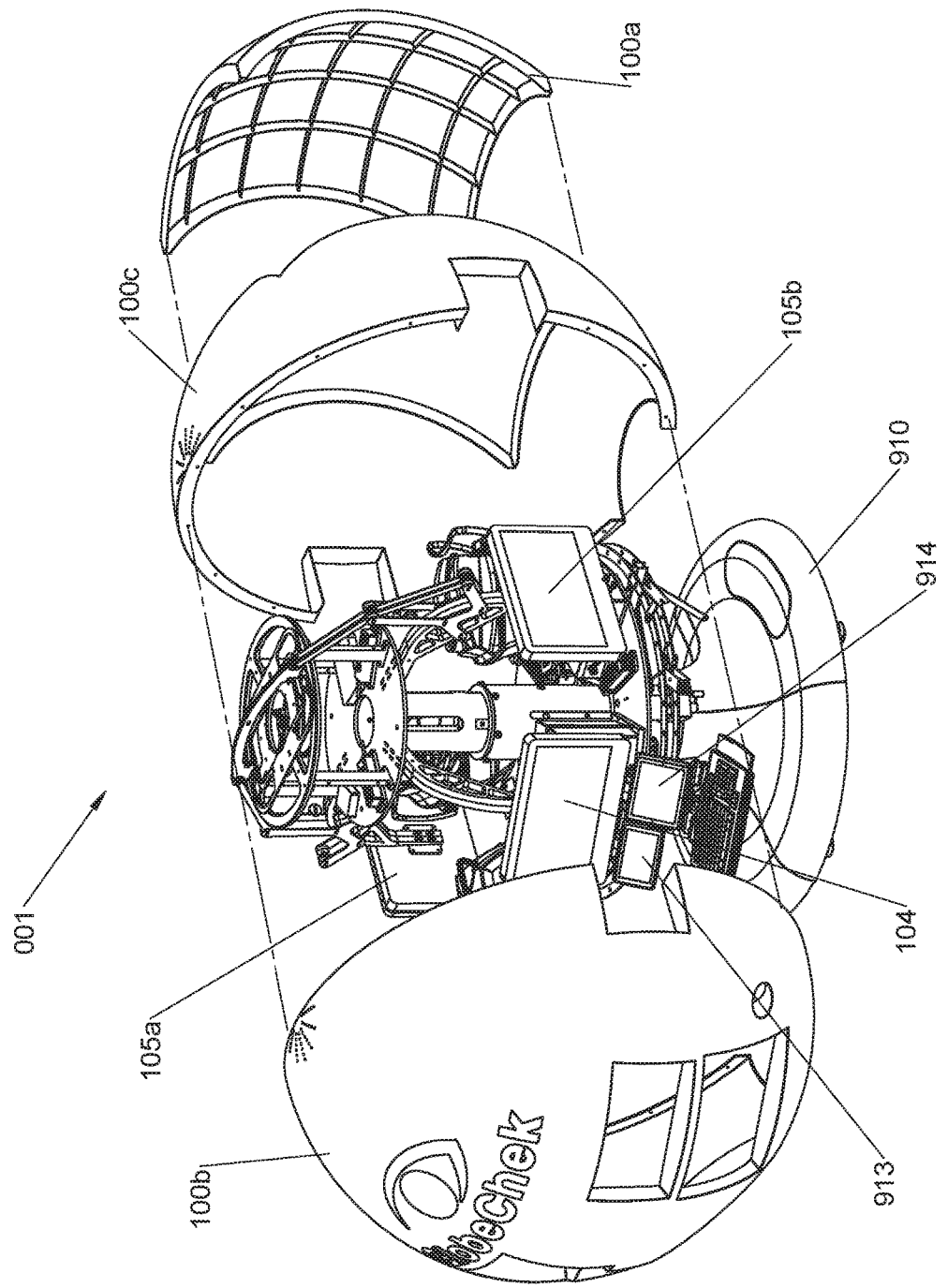
FIG. 4 depicts an exploded perspective view of an embodiment of the eye examination kiosk of the invention.

Referring now to FIG. 4, a perspective view of an embodiment of eye examination kiosk 001 is depicted. The outer shell 100 may be comprised of any number of sections that together make up a complete shell, which may be of any geometric shape. In the embodiment shown, the shape of outer shell 100 is spherical and may comprise portions 100*b* and 100*c* that are adapted to be attached by any means known in the mechanical arts such as such as threaded fasteners, rivets, complementary locking structures, chemical bonding or any other known means for mechanical assembly, but may be preferably be attached by threaded fasteners, and shell portion 100*a*, which is removable from shell 100 to allow access for maintenance, inspection or cleaning of eye examination kiosk 100. Displays 104, 105*a*, 105*b*, 913 and 914 are shown for reference. Leg cover 910 is also shown for reference.

Figure 5:
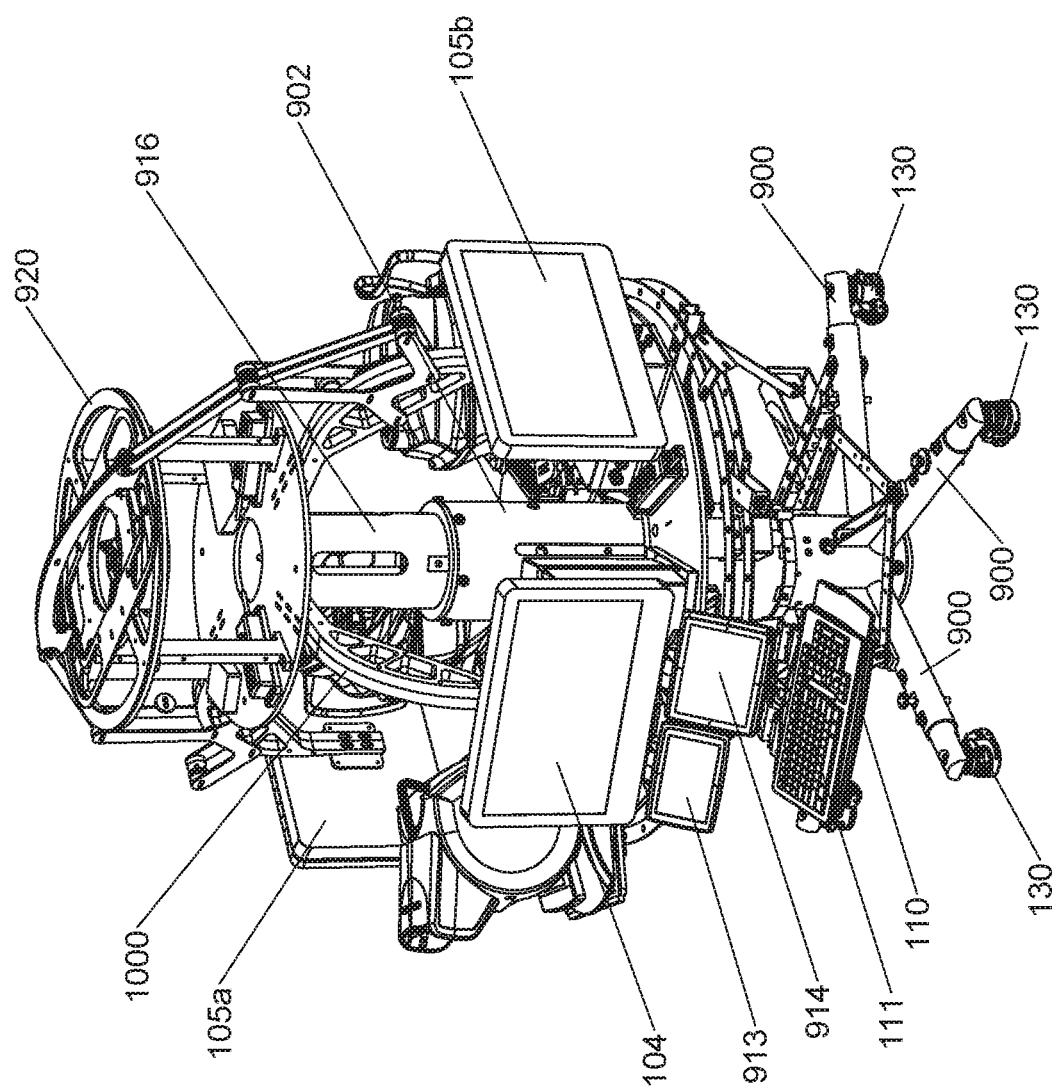
FIG. 5 depicts an internal perspective view of an embodiment of the eye examination kiosk of the invention in which the outer shell and eye examination devices are not shown.
Figure 11:
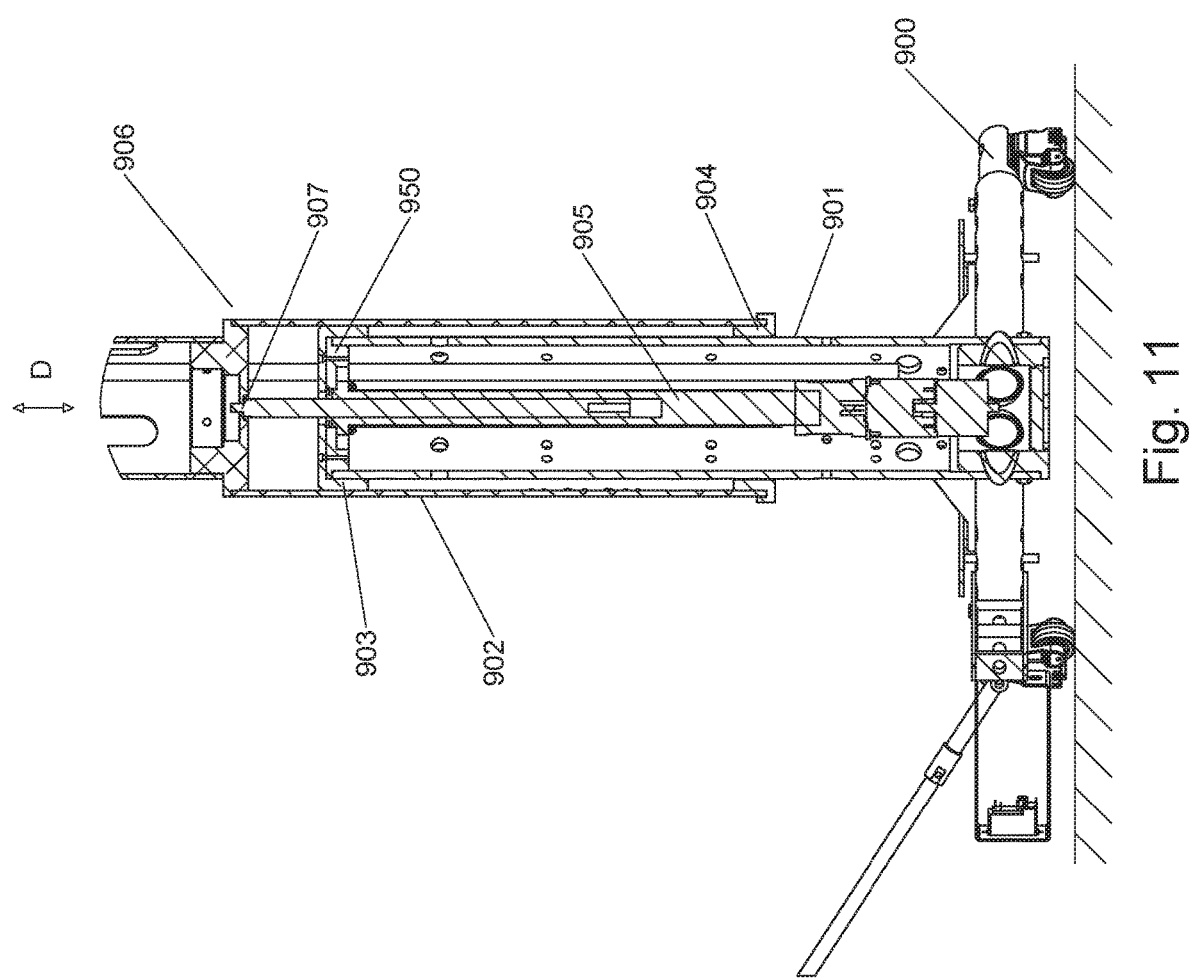
FIG. 11 depicts a side cross section view of an embodiment of the vertical lift assembly of the invention.
Figure 12:
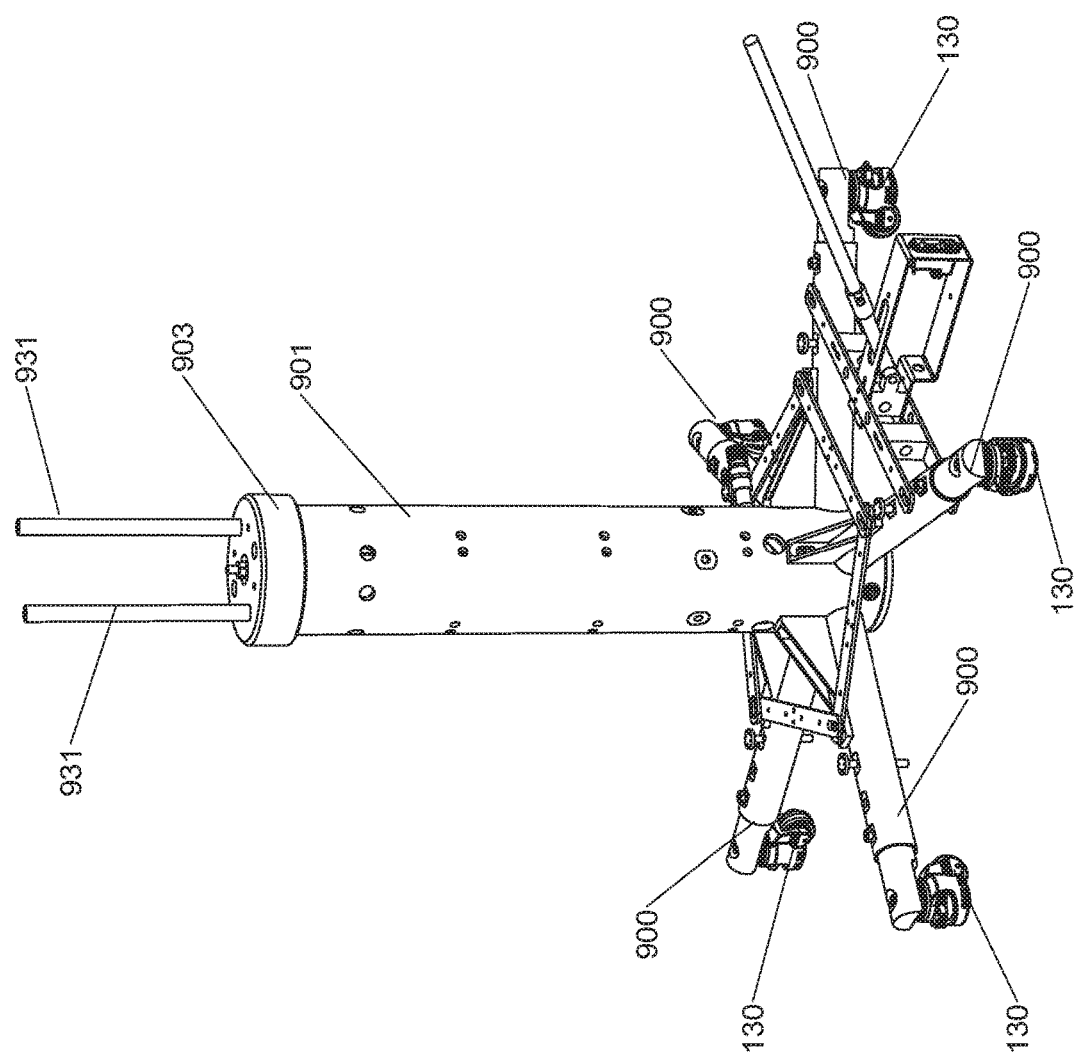
FIG. 12 depicts a perspective view of the legs and casters and an embodiment of the support structure for same.

Referring now to FIG. 5, an internal perspective view of an embodiment of the eye examination kiosk of the invention, in which the outer shell and eye examination devices are not shown, is depicted. Displays 105*a*, 105*b* and 104, as well as shell 100, as well as internal support structure 920, may be attached directly or indirectly to kiosk internal structure 916 via intermediate mechanical structure. Kiosk internal structure 916 may be attached to a tube 920 of the kiosk vertical lift assembly as is shown in FIG. 11 such that it, and displays 104, 105*a* and 105*b*, displays 913 and 914, and keyboard 911 and keyboard shelf 910, as well as shell 100 and internal support structure 920, are translated up or down by the operation of vertical lift actuator 905. Legs 900 and optional casters 130 are shown for reference. Legs 900 are attached, directly or indirectly, to tube 901 as shown in FIG. 11, and thus do not translate upward with the extension of actuator 905, but remain resting upon support surface 002 or remain in a rolling engagement with support surface 002 by the operation of casters 130.

Figure 6:
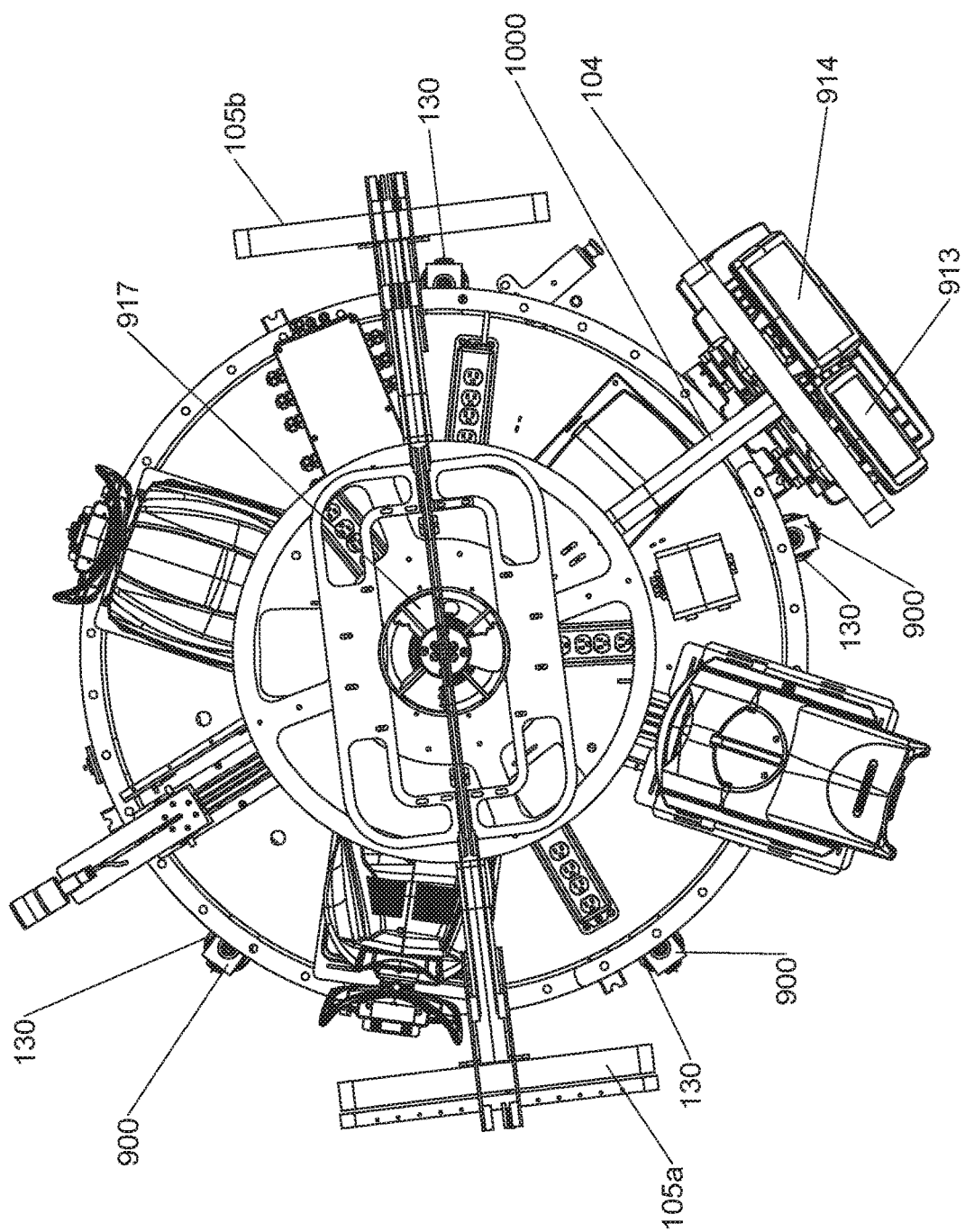
FIG. 6 depicts an internal top view of an embodiment of the eye examination kiosk of the invention in which the outer shell and eye examination devices are not shown.
Figure 7:
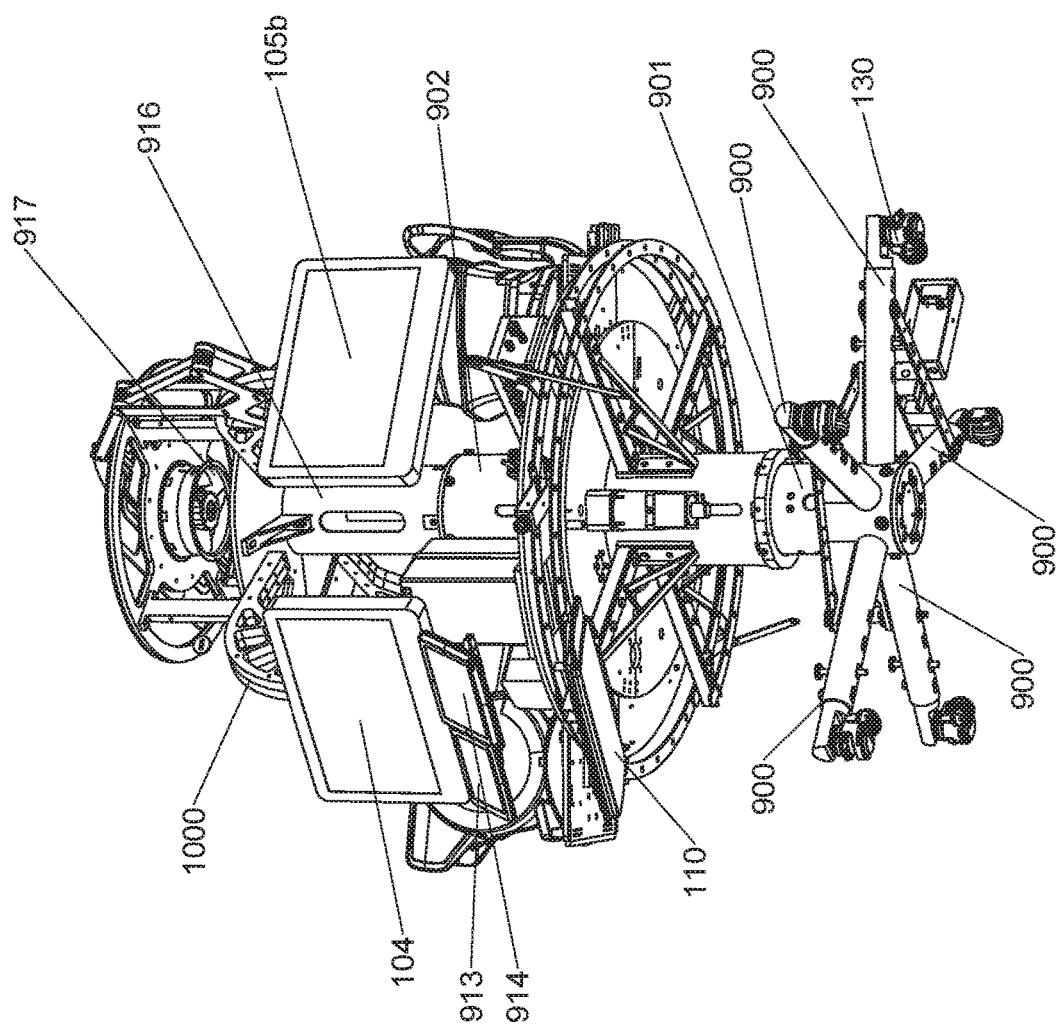
FIG. 7 depicts an internal perspective view, from underneath, of an embodiment of the invention. In this view, the outer shell and eye examination equipment of the invention are not shown.

Referring now to FIGS. 6 and 7, top and underneath perspective views, respectively, of an embodiment of the invention. In these figures, the outer shell 100 of the invention is not shown. Displays 104, 105*a*, 105*b* 913 and 914 are depicted attached to intermediate structure 1000, which is attached directly or indirectly to structure 916, which is in turn attached to tube 902 that is translated up or down in a sliding engagement on tube 901 as is further depicted in FIG. 11. Legs 900 and casters 130 are depicted for reference. Fan 917 may be utilized to draw air into the outer shell 100, or exhaust air from outer sell 100, in order to provide cooling to the internal electronic components of the eye examination kiosk.

At least one, but preferably a plurality, of eye examination devices such as, for example 200, 201, 202, and other eye examination device may be attached, or mounted, to an upper surface of rotable table 108 either directly or by way of an intermediary linear actuator and slide that is controllable for translating the eye examination devices towards or away from a patient.

Figure 8:
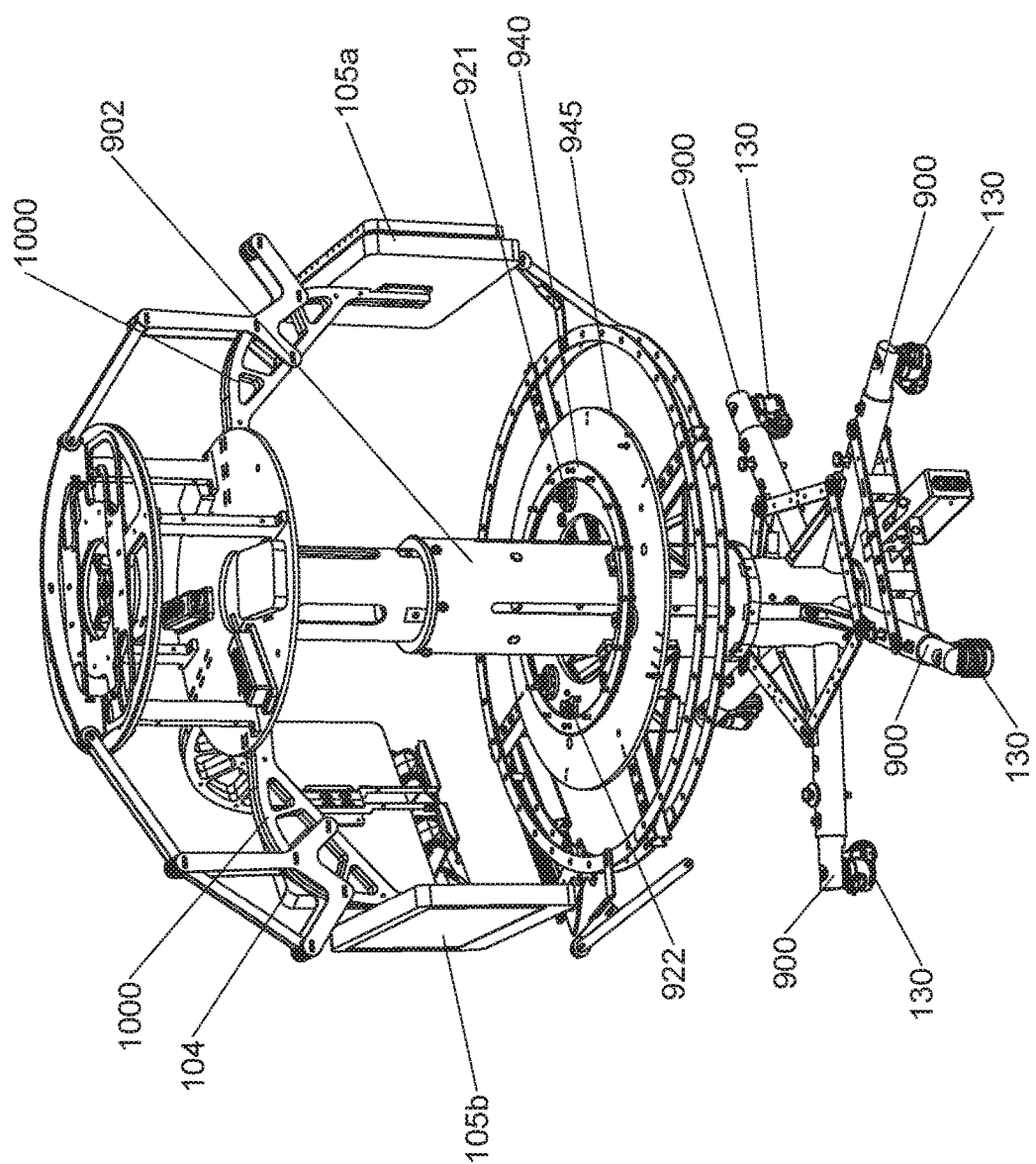
FIG. 8 depicts an internal perspective view of an embodiment of the invention in which eye examination equipment is not shown. In this view, the outer shell of the invention is not shown.

Referring now to FIG. 8, an internal perspective view of an embodiment of the invention is depicted in which eye examination device is not shown. In this view, the outer shell of the invention is not shown. Displays 104, 105*a*, and 105*b* are depicted attached to intermediate structure 1000, which is attached directly or indirectly to structure 916, which is in turn attached to tube 902 that is translated up or down in a sliding engagement on tube 901 as is further depicted in FIG. 11. Legs 900 and casters 130 are depicted for reference.

Support plate 945 and rotary table drive ring 940 are depicted for reference, as well as are rotary drive motor 922 and thrust bearings 921.

In the embodiment depicted in the figures, rotable table 108 is rotable in direction B about axis A. The rotation of rotable table 108 is such that any of eye examination devices are 200, 201, and 202, rotated about axis A into a predefined position in order to perform an eye examination on a patient. Such rotation may be controlled by the controller (not shown in FIG. 8) either automatically or using instructions from the kiosk operator input into the controller using keyboard 111 (not shown in FIG. 8), joystick 114 (not shown in FIG. 8), mouse 112 (not shown in FIG. 8) or any other input device attached to the controller. For instance, in an embodiment, a microphone may be attached to the controller so that the kiosk operator may speak voice commands into the microphone which may be interpreted by the controller in order to carry out steps and functions of the invention.

Figure 9:
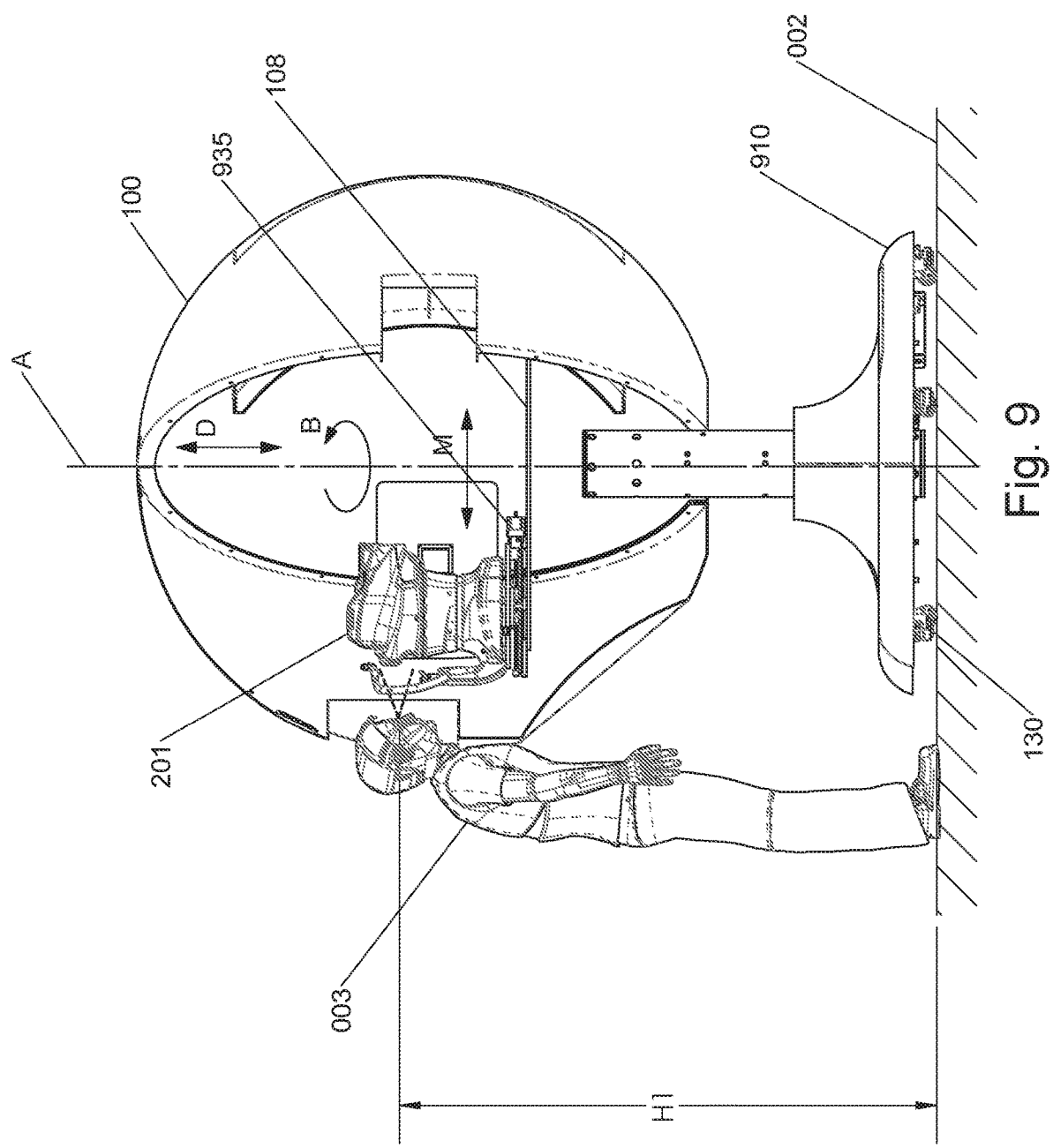
FIG. 9 depicts a side view of an embodiment of the eye examination kiosk of the invention in which the eye examination kiosk has been raised to accommodate eye examination of a tall standing person. The eye examination kiosk is depicted in a raised position.

Referring now to FIG. 9, a side view of an embodiment of the eye examination kiosk of the invention is depicted in which the eye examination kiosk has been raised in a direction of arrow D to accommodate eye examination of a standing patient 003 at an eye height H1 above support surface 002. The eye examination kiosk is thus depicted in a raised position. In this example, the operation of the vertical lift assembly shown in FIG. 11 has raised the outer shell 100, rotary table 108, and eye examination device 201 from a lowered position to a raised position H1 along axis A by extension of the vertical lift actuator 905, which extension may be commanded by an operator through keyboard, touch screen, voice or other command to controller 700 (not shown in FIG. 9). Rotary table 108 has been commanded by controller 700 to rotate about axis A in a direction of arrow B such that eye examination device 201 is located within examination opening 121, so that patient 003 may lean forward into examination opening 121 to present their eyes for examination to eye examination device 201. Eye examination device 201 has been translated on controllable actuator and slide 935 in direction M so as to be in proximity with the eye of patient 003, enabling eye examination of patient 003's eye or eyes.

Figure 10:
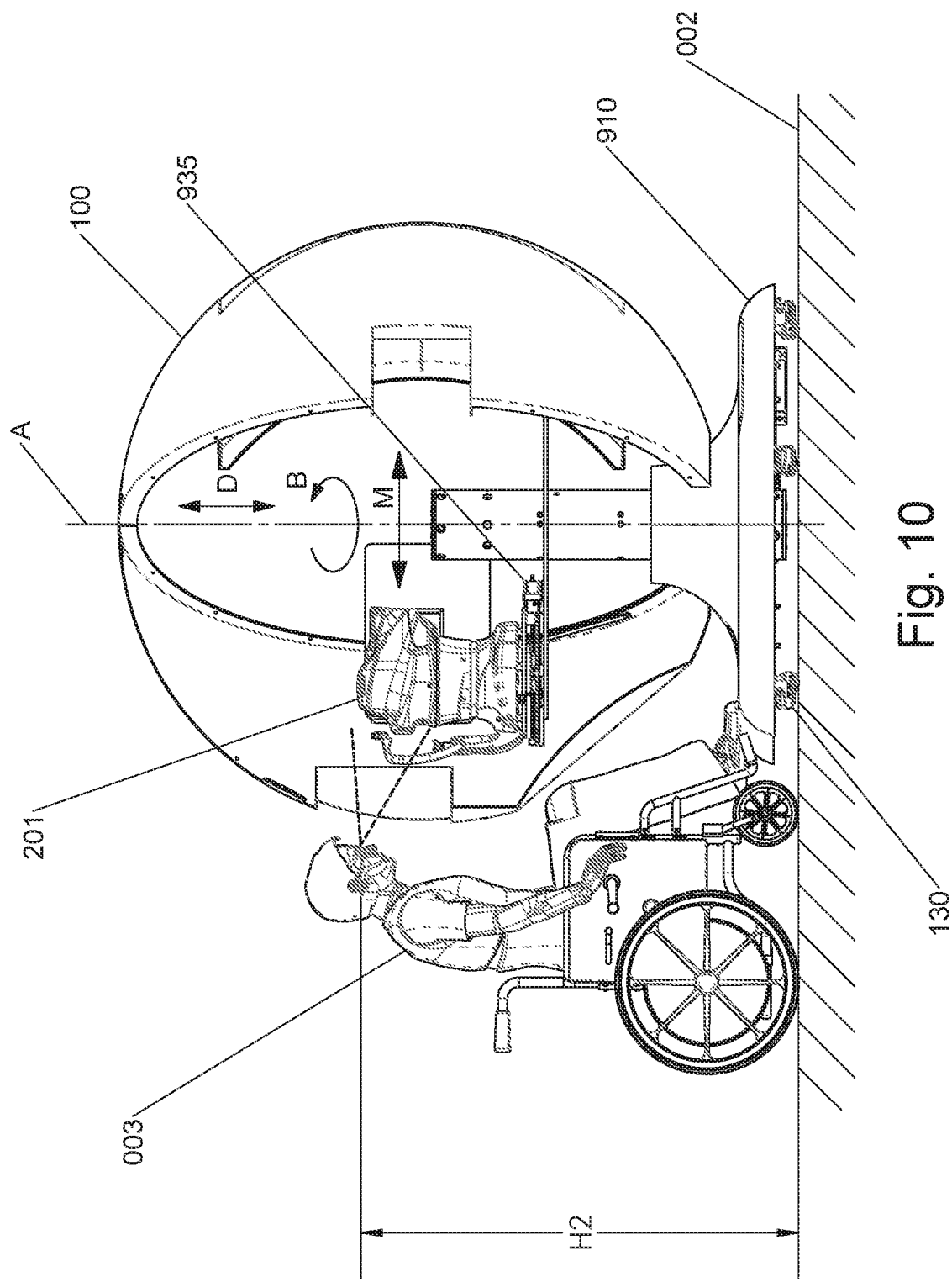
FIG. 10 depicts a side view of an embodiment of the eye examination kiosk of the invention in which the eye examination kiosk has been lower to accommodate eye examination of a patient who is sitting in a wheelchair, scooter or other mobility device. The eye examination kiosk is depicted in a lowered position.

Referring now to FIG. 10, a side view of an embodiment of the eye examination kiosk of the invention is depicted in which the eye examination kiosk has been lowered in a direction of arrow D to accommodate eye examination of a patient 003 sitting in a wheelchair, scooter or mobile assistance device, presenting an eye height H2 above support surface 002. The eye examination kiosk is thus depicted in a lowered position. In this example, the operation of the vertical lift assembly shown in FIG. 11 has lowered the outer shell 100, rotary table 108, and eye examination device 201 from a raised position to a lowered position H2 along axis A by retraction of the vertical lift actuator 905, which retraction may be commanded by an operator through keyboard, touch screen, voice or other command to controller 700 (not shown in FIG. 9). Rotary table 108 has been commanded by controller 700 to rotate about axis A in a direction of arrow B such that eye examination device 201 is located within examination opening 121, so that patient 003 may lean forward into examination opening 121 to present their eyes for examination to eye examination device 201. Eye examination device 201 has been translated on actuator and slide 935 in direction M so as to be in proximity with the eye of patient 003, enabling eye examination of patient 003's eye or eyes.

Referring now to FIG. 11, a side cross section view of an embodiment of the vertical lift assembly of the invention is depicted. The vertical lift assembly is adapted to lift said rotary table and said outer shell to accommodate patients with differing eye examination heights, the eye examination defined as the distance from support surface 002 to the patient's line of sight. The vertical lift assembly is further may have a first tube 901 having a first axis slidingly engaged with a second tube 902 having a second axis, wherein the first axis the said second axis are coaxial with axis A. The sliding engagement between first tube 901 and second tube 902 may be provided by bearings 903 and 904, which may be any material that that provides a low enough coefficient of frictions so as to allow first tube 901 and second tube 902 to slide along one another along the first and second axes, one tube within the other. Bearings 903 and 904 may be constructed, for example, of Teflon®, Delrin and like materials. The vertical lift assembly further comprises a vertical lift actuator 905 that has a first end and a second end, the first end attached to first tube 901, for example, via tube end cap 950, and the second end attached to second tube 902 at plate 906, the actuator disposed such when it extends, second tube 902 is translated on the sliding engagement along inner tube 901 in a first axial direction along axis A, and when actuator 905 retracts, the outer tube 902 is translated on the sliding engagement along inner tube 901 in a second axial direction along axis A. Actuator 905 may be in communication with controller 700 so that controller 700 may command actuator 905 to extend or retract. Rotary table 108 and outer shell 100 (not shown in FIG. 11) are attached either directly or indirectly to second tube 902. Legs 900 may be attached to first tube 901. Thus, in an exemplary embodiment, when actuator 905 is extended, rotary table 108 and said outer shell 100 are translated in an upward direction, away from support surface 002, and when actuator 905 is retracted, rotary table 108 and outer shell 100 are translated in a downward direction, towards support surface 002. This operation of the vertical lift assembly allows an operator to command the eye examination kiosk to raise or lower the eye examination device so as to be alignable with the eye of patients of differing heights. In the embodiment shown, first tube 901 is of smaller outer diameter than second tube 902, and slides within tube 902 on bearings 903 and 904. In other embodiments, tube 902 may slide within tube 901. Likewise, in other embodiments, the cross section of tubes 901 and 902 may take any cross sectional shape. They need not be of circular cross section, nor do they need to be of a closed cross section. Thus, tubes 901 and 902 may be of circular cross section but they may also be of square or rectangular cross section, or they may be of an I-shaped cross section or any other cross section.

Figure 13:
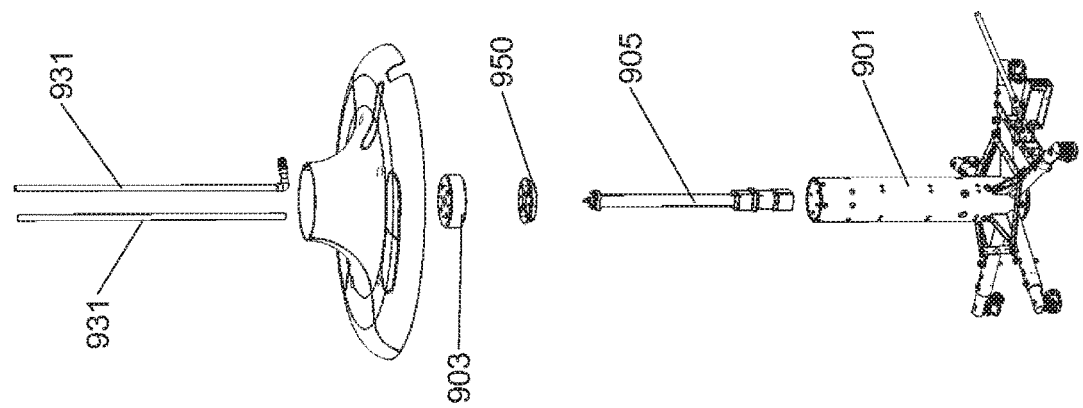
FIG. 13 depicts a perspective view of the legs and casters and an embodiment of the support structure for same, also showing the leg cover and cable snorkel.
Figure 14:
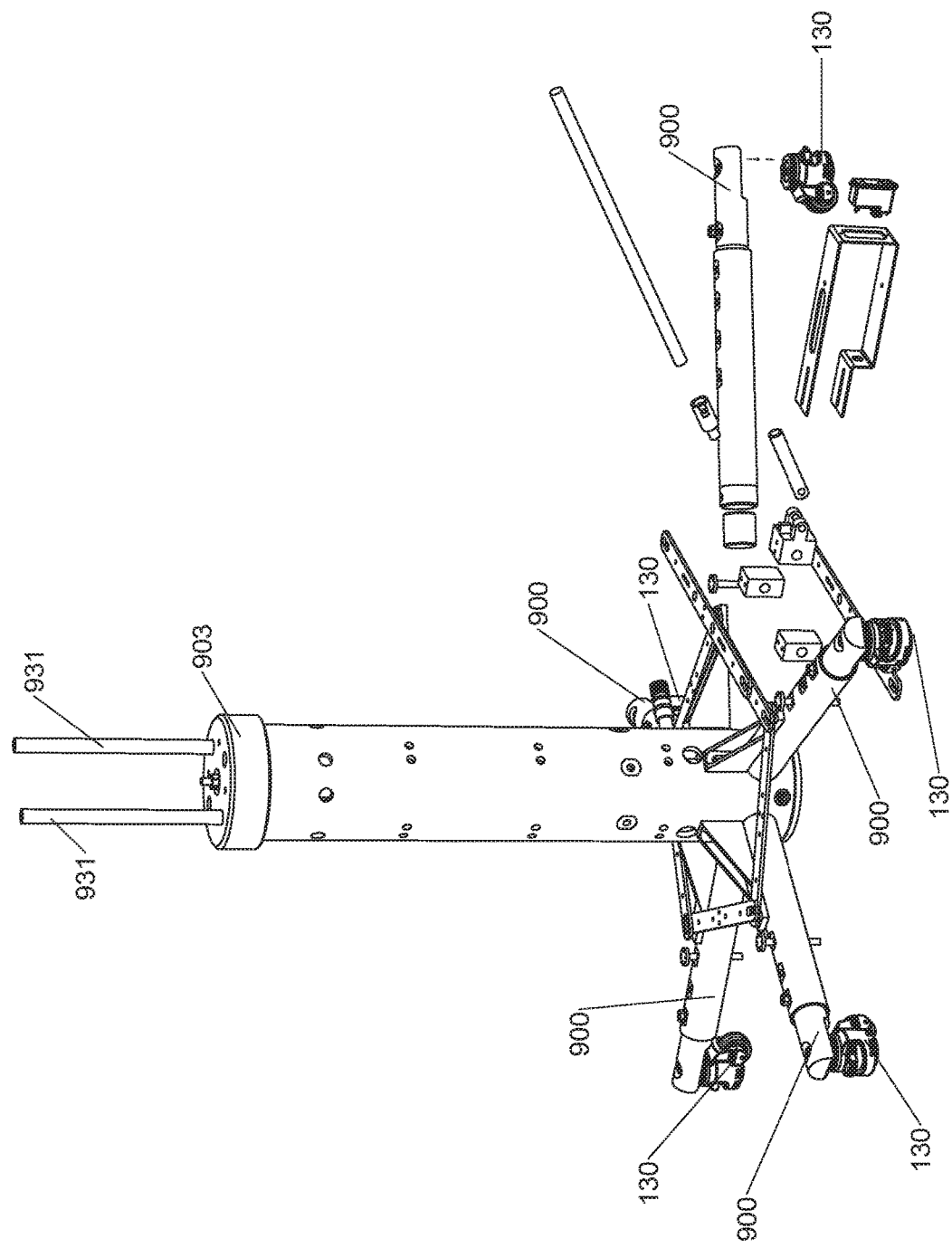
FIG. 14 depicts a partially exploded, perspective view of the legs and casters and an embodiment of the support structure for same.
Figure 15:
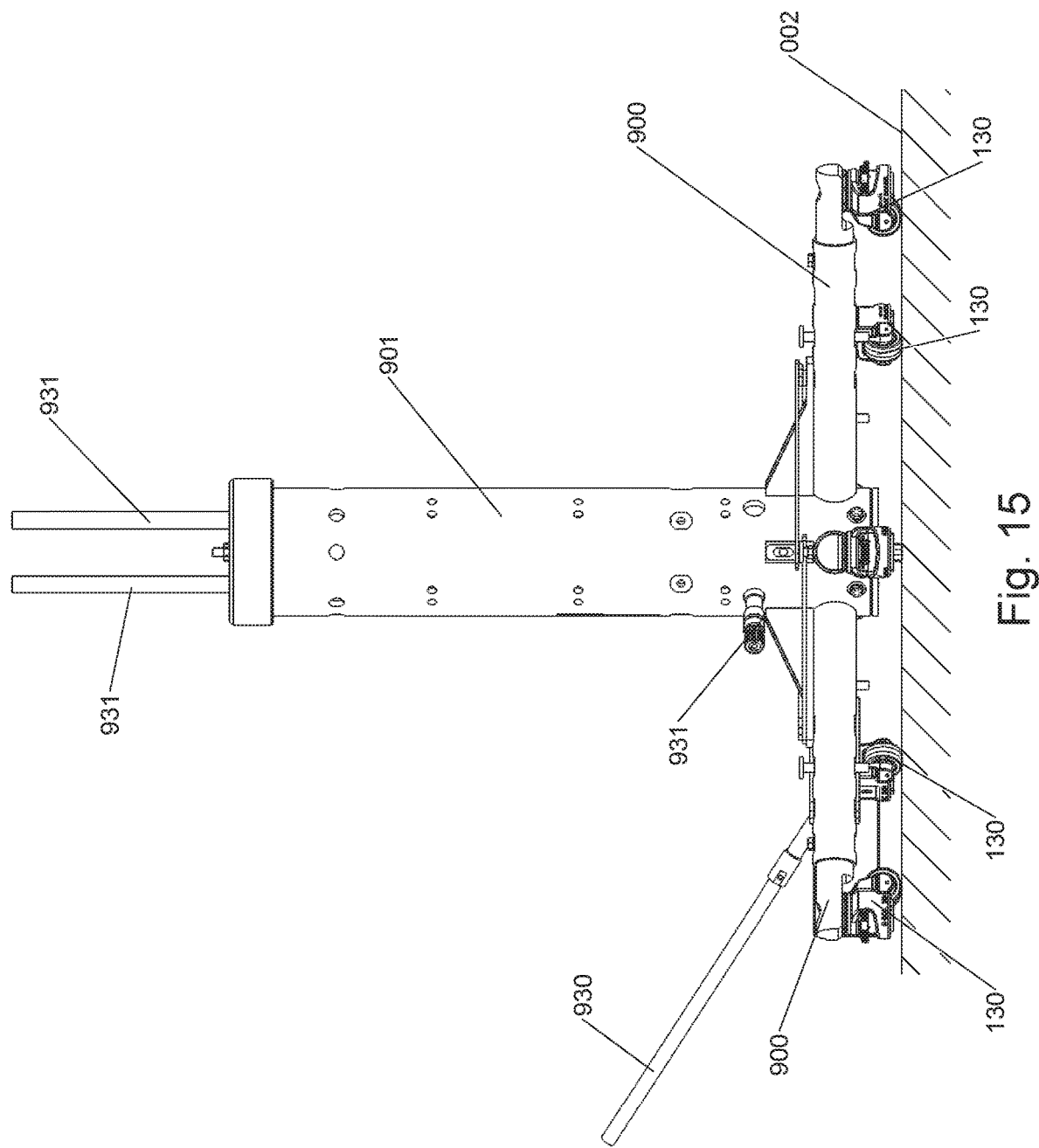
FIG. 15 depicts a perspective view of the legs and casters and an embodiment of the support structure for same, also showing the leg cover and cable snorkel.
Figure 16:
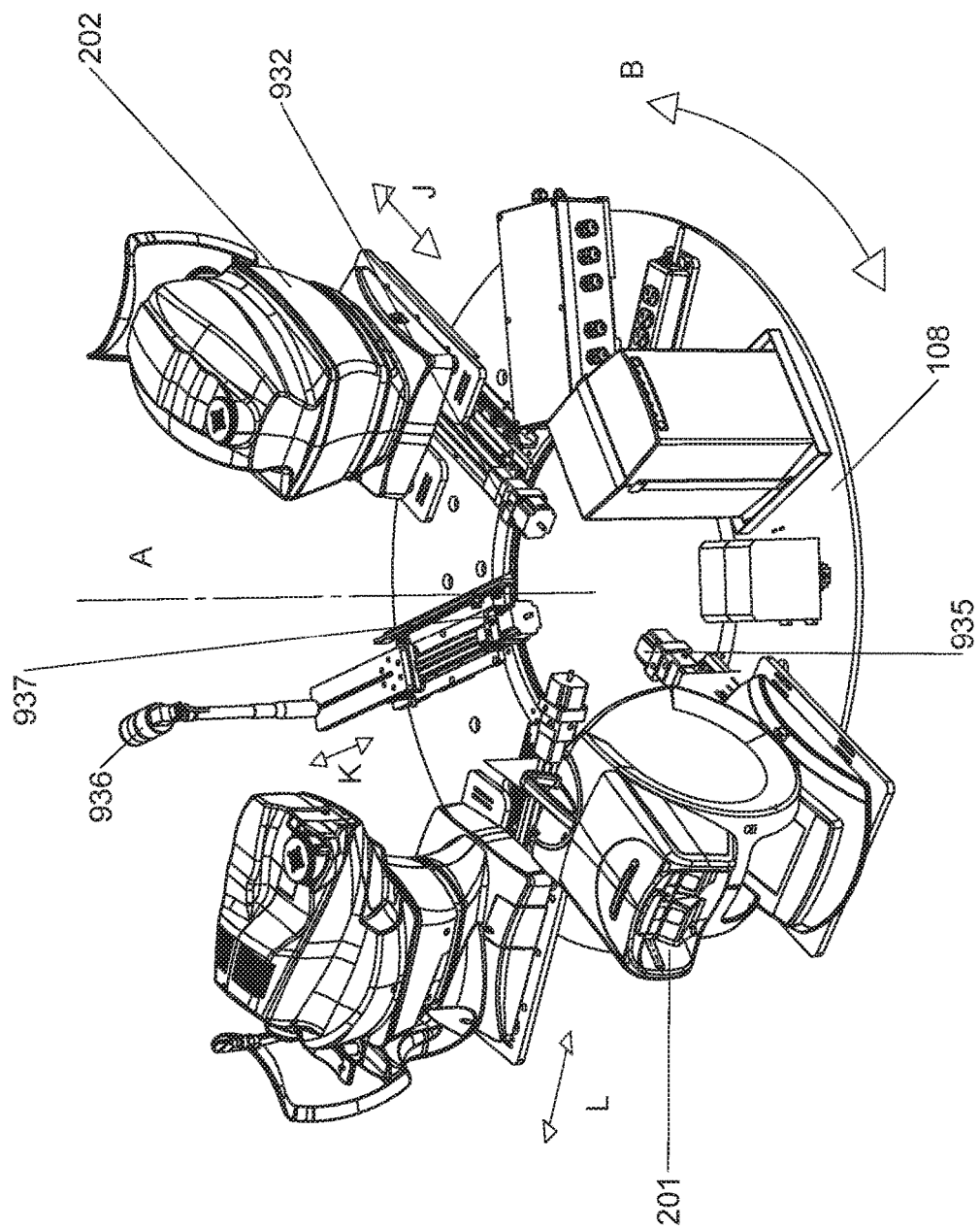
FIG. 16 depicts a perspective view of an embodiment of the invention in which eye examination devices are mounted to a rotable table. In this view, the kiosk outer shell is not shown. The rotable table is rotable about axis A in direction B, and certain eye examination equipment may be translatable upon rotable table 108 as depicted arrows M, L, and J.
Figure 17:
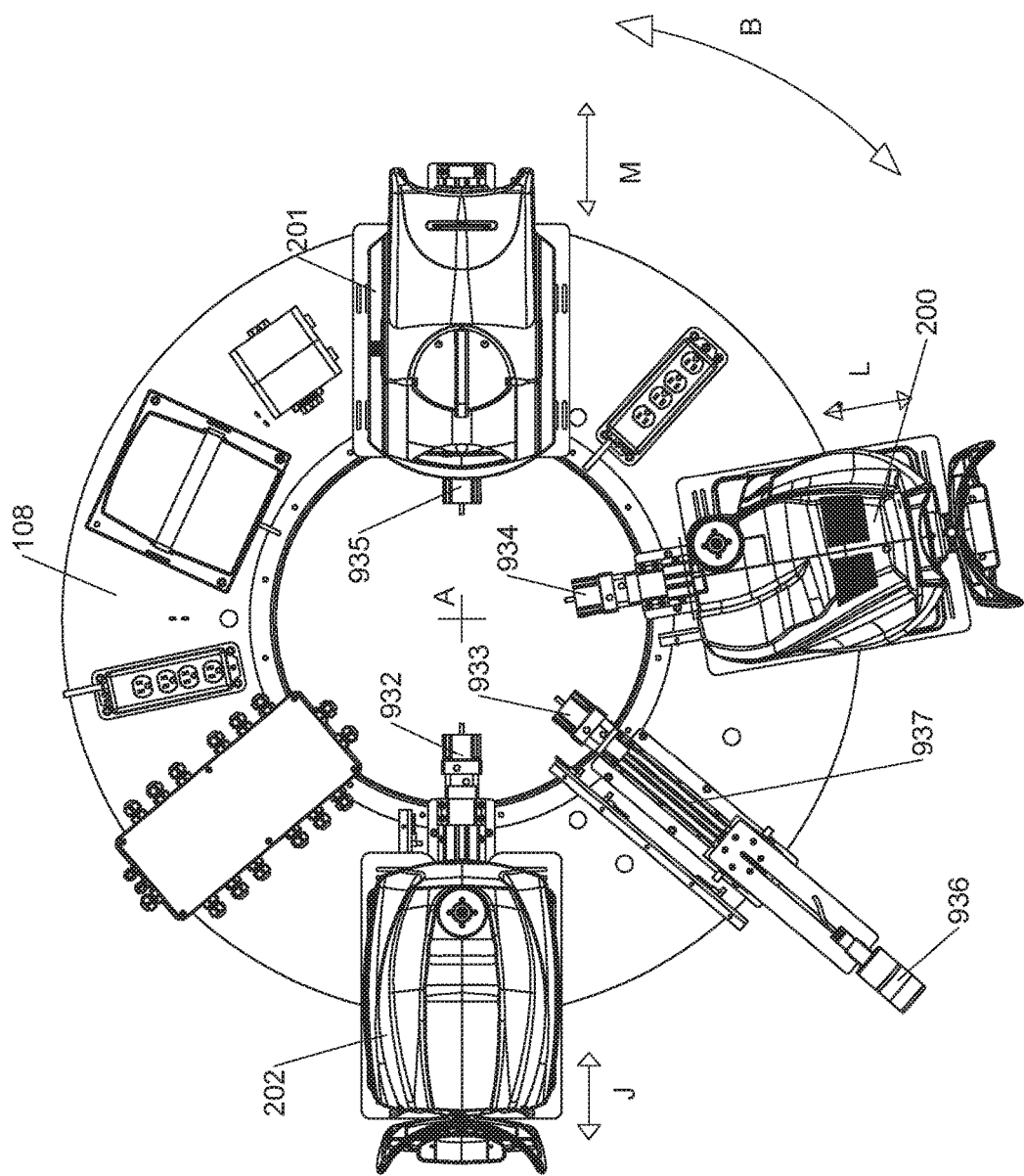
FIG. 17 depicts a perspective view of an embodiment of the invention in which eye examination devices are mounted to a rotable table. In this view, the kiosk outer shell is not shown. The rotable table is rotable about axis A in direction B, and certain eye examination device may be translatable as depicted arrows M, L, and J.
Figure 18:
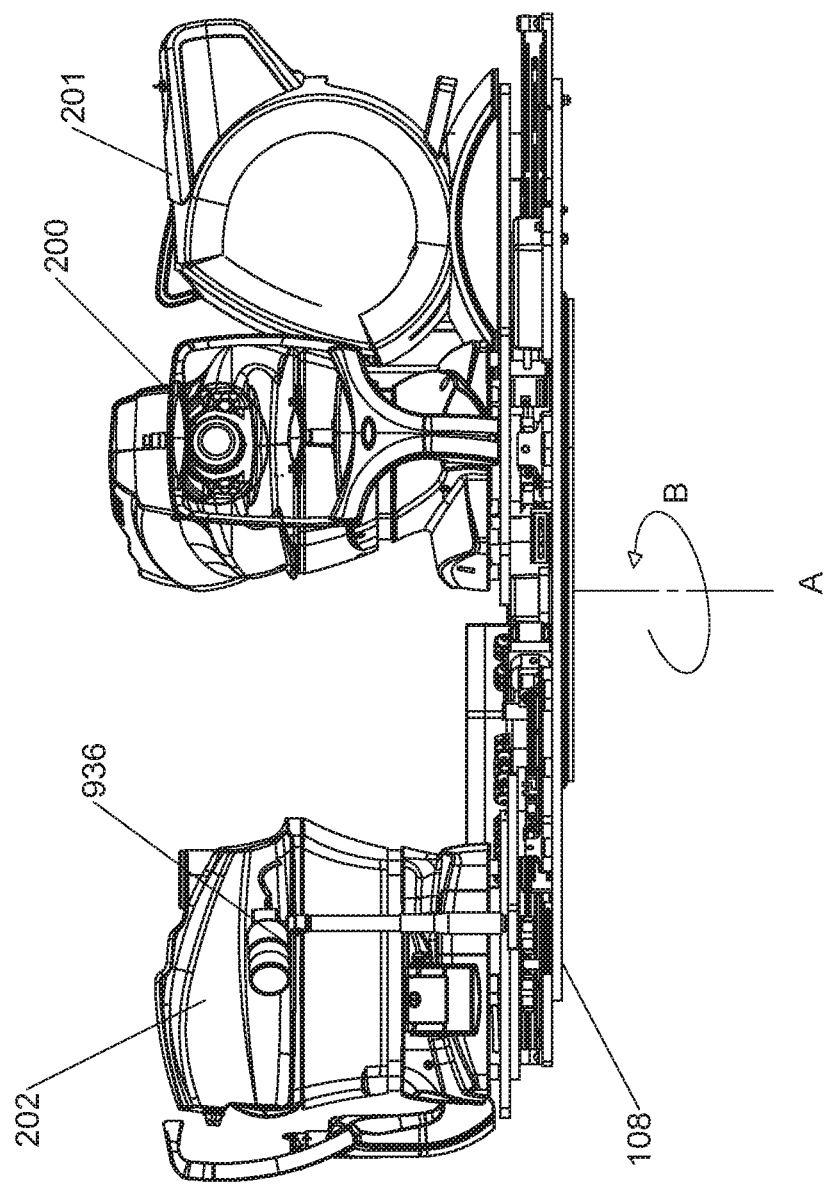
FIG. 18 depicts a side view of an embodiment of the invention in which eye examination devices are mounted to a rotary table. In this view, the kiosk outer shell is not shown. The rotary table is rotable about axis A in direction B.
Figure 19:
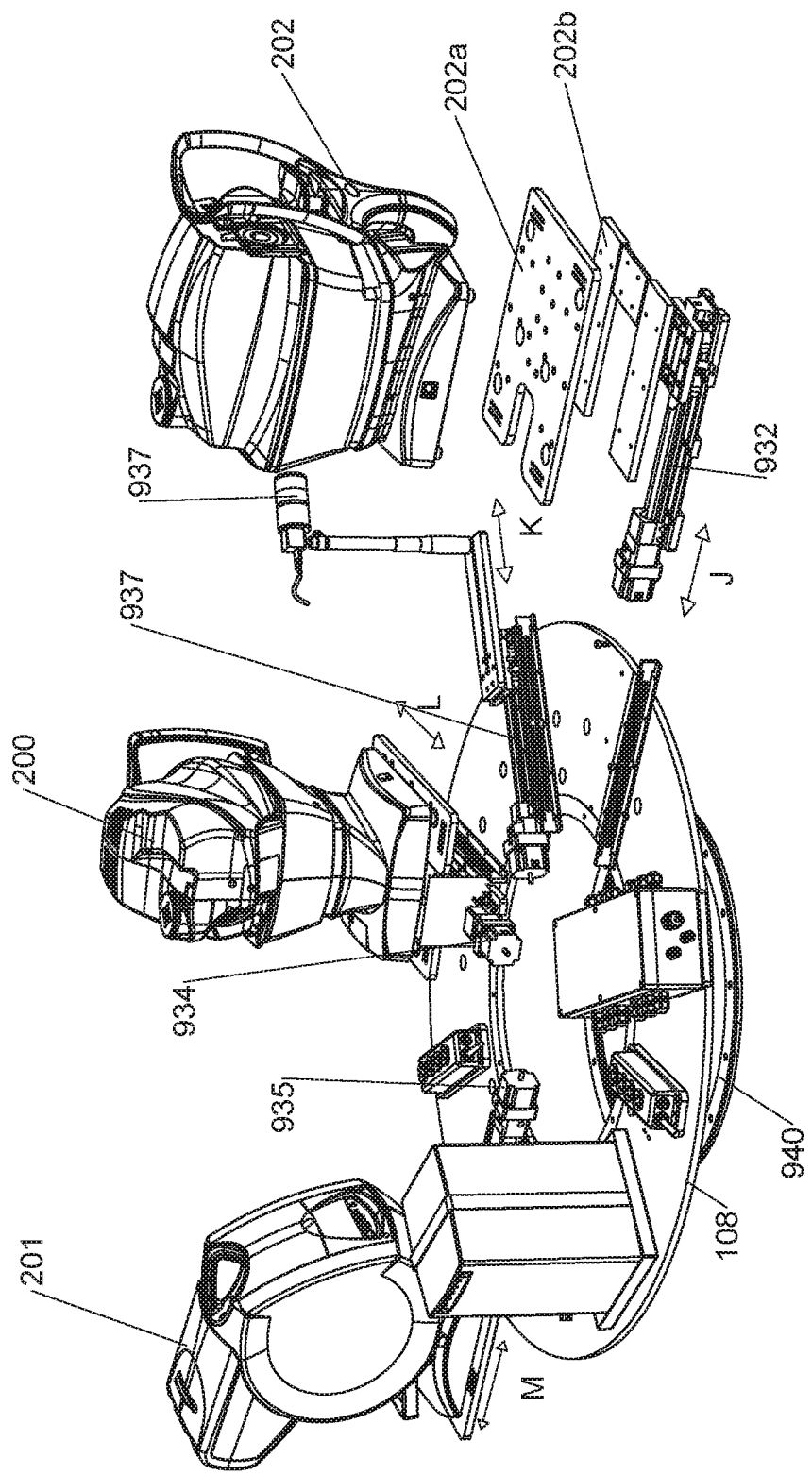
FIG. 19 depicts a perspective view of an embodiment of the invention in which eye examination devices are mounted to a rotary table. In this view, the kiosk outer shell is not shown. Certain eye examination device may be translatable as depicted arrows M, L, and J. The actuator and slide assembly allowing translation of the eye examination devices is shown in exploded view.

Referring now to FIGS. 12, 13, 14, and 15, views of the legs and casters and an embodiment of the support structure for same, also showing the leg cover 910 and cable snorkel 931 are depicted. Vertical lift assembly first tube 901 is attached to legs 900, which may comprise casters 130 to create a rolling engagement between the eye examination kiosk of the invention and support surface 002 (shown in FIG. 15). The invention may comprise one or more cable snorkel(s) 931 to protect cabling for power and electronic signals that is routed through the snorkeling and up into the support structure 920 or other support structure (not depicted in FIG. 12, 13, 14, or 15). Vertical lift actuator 905, bearing 903 and tube end cap 950 are depicted in FIG. 13 for reference.

Referring now to FIGS. 16, 17, 18 and 19, the kiosk outer shell is not shown. At least one examination device such as 200, 201 or 202 are attached to the rotable table 108, either directly or by way of actuator and slide assemblies 934, 935 and 932, respectively. The rotable table 108 is rotable about axis A in direction B by the rotary drive assembly shown in FIGS. 21A and 21B, and the eye examination devices may be translatable by way of actuator and slide assemblies 934, 935 and 932 as depicted arrows L, M, and J. Each of the actuator and slide assemblies 933, 934, 935 and 932 are in communication with and controllable by controller 700. Thus, each of the actuator and slide assemblies may be commanded by controller 700 to extend or retract, moving the respective eye examination device 200, 201 or 202 closer to, or further away from, axis A. The eye examination kiosk of the invention may also comprise a still or video camera 936 which may be used for taking any desired still or video images but may be used as a means for capturing photographs of a patient for transmittal along with other patient information and examination results to a remote server or other user. The attachment between any of the eye examination devices 200, 201, 202 and camera 936 and said rotary table 108 may include the actuators and slide assembly 933, 934, 935 and 932. The slides may be translatable by the actuators upon command from controller 700 such that each eye examination device and the camera 936 are controllably translatable towards or away from said outer shell by command from the controller 700. Controllable rotary table motor 922 (see FIG. 20) may be in communication with controller 700, and controller 700 may be in communication with non-transitory physical computer readable media containing computer readable instructions for rotating said rotary table rotable to predefined points of rotation, one predefined points of rotation for each eye examination device, such that each of the plurality of eye examination devices is presented to a patient for eye examination of the patient such that the predefined axis of the eye examination device is located coincident with the eye of a patient when rotable table 108 is commanded by said controller to rotate to the predefined point of rotation for a specific eye examination device. The predefined point of rotation of rotable table 108 are each located at the examination opening 121.

Figure 20:
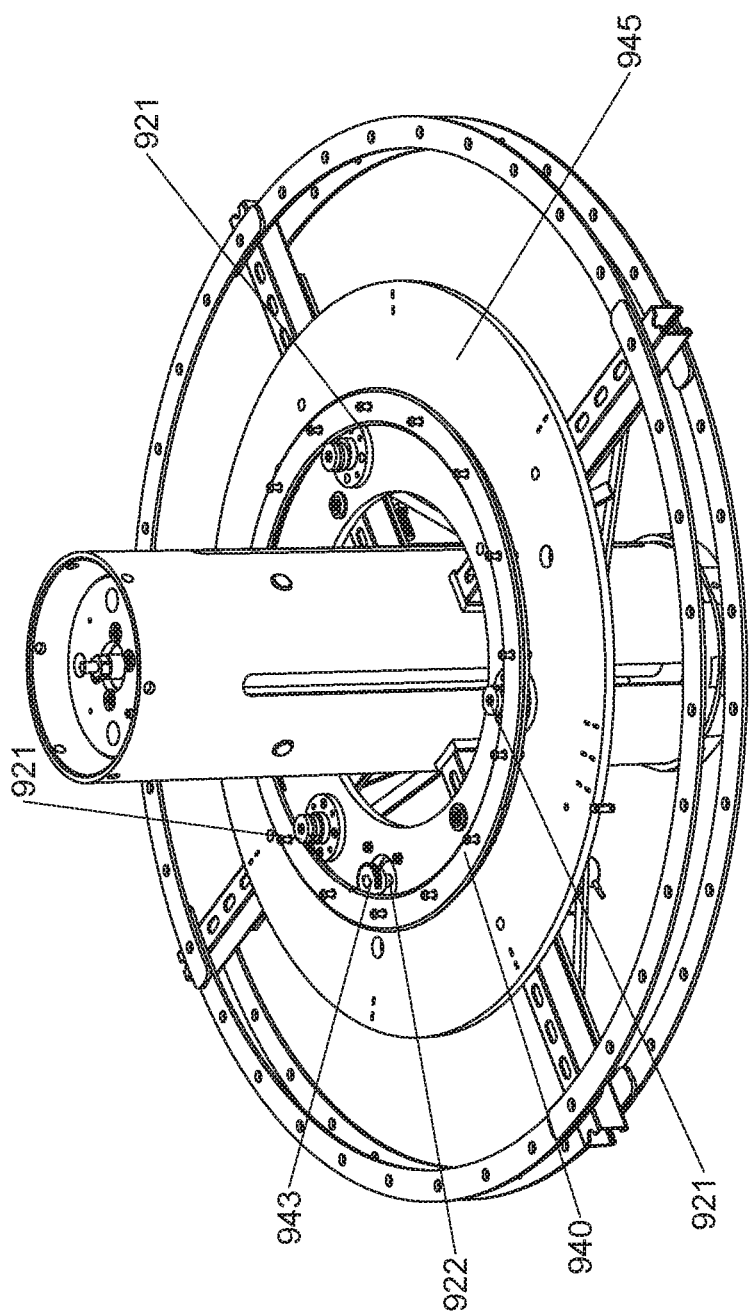
FIG. 20 depicts a perspective view of a portion of the rotary drive assembly of an embodiment of the invention.

Referring now to FIG. 20, a perspective view of a portion of the rotary drive assembly of an embodiment of the invention is depicted. Rotary table drive ring 940 is attached to a surface, such as an upper surface, of support plate 945. A plurality of thrust bearings support rotary table drive ring 940 in a complimentary V-groove rolling engagement, allowing rotary table drive ring 940 to rotate when controllable rotary table motor 922, which is in communication with controller 700, is commanded by controller 700 to rotate, causing rotary drive gear 943, which comprises gear teeth that are engaged with complimentary gear teeth in rotary gear ring 944 (shown in FIG. 21), to rotate about axis A. Rotary gear ring 944 is attached to a surface, such as a lower surface, of rotary table drive ring (shown in FIG. 21).

Referring now to FIGS. 21A and 21B, cross section views of a portion of the rotary drive assembly of an embodiment of the invention is depicted. Rotary table drive ring 940 is attached to a surface, such as an upper surface, of support plate 945. A plurality of thrust bearings support rotary table drive ring 940 in a complimentary V-groove rolling engagement, allowing rotary table drive ring 940 to rotate when controllable rotary table motor 922, which is in communication with controller 700, is commanded by controller 700 to rotate on axis G as shown by arrow H, causing rotary drive gear 943, which comprises gear teeth that are engaged with complimentary gear teeth in rotary gear ring 944 (shown in FIG. 21), to rotate about axis A. Rotary gear ring 944 is attached to a surface, such as a lower surface, of rotary table drive ring (shown in FIG. 21). Thrust bearings 921 may be adapted by internal bearings to rotate on axis E as shown by arrow F while supporting the load applied on rotary table drive ring 940. In operation, support plat 945 does not rotate; the operation of controllable rotary table motor 922 causes the rotation of rotary drive gear 943, which, through its toothed engagement with rotary gear ring 944, causes rotary table drive ring 940 and thus rotary table 108 to rotate about axis A as shown by arrow B when commanded by controller 700. V-groove 946, which is complimentary as between thrust bearings 921 and rotary table drive ring 940, enables rotary table drive ring 940 to support the load applied by rotary table 108.

Figure 22:
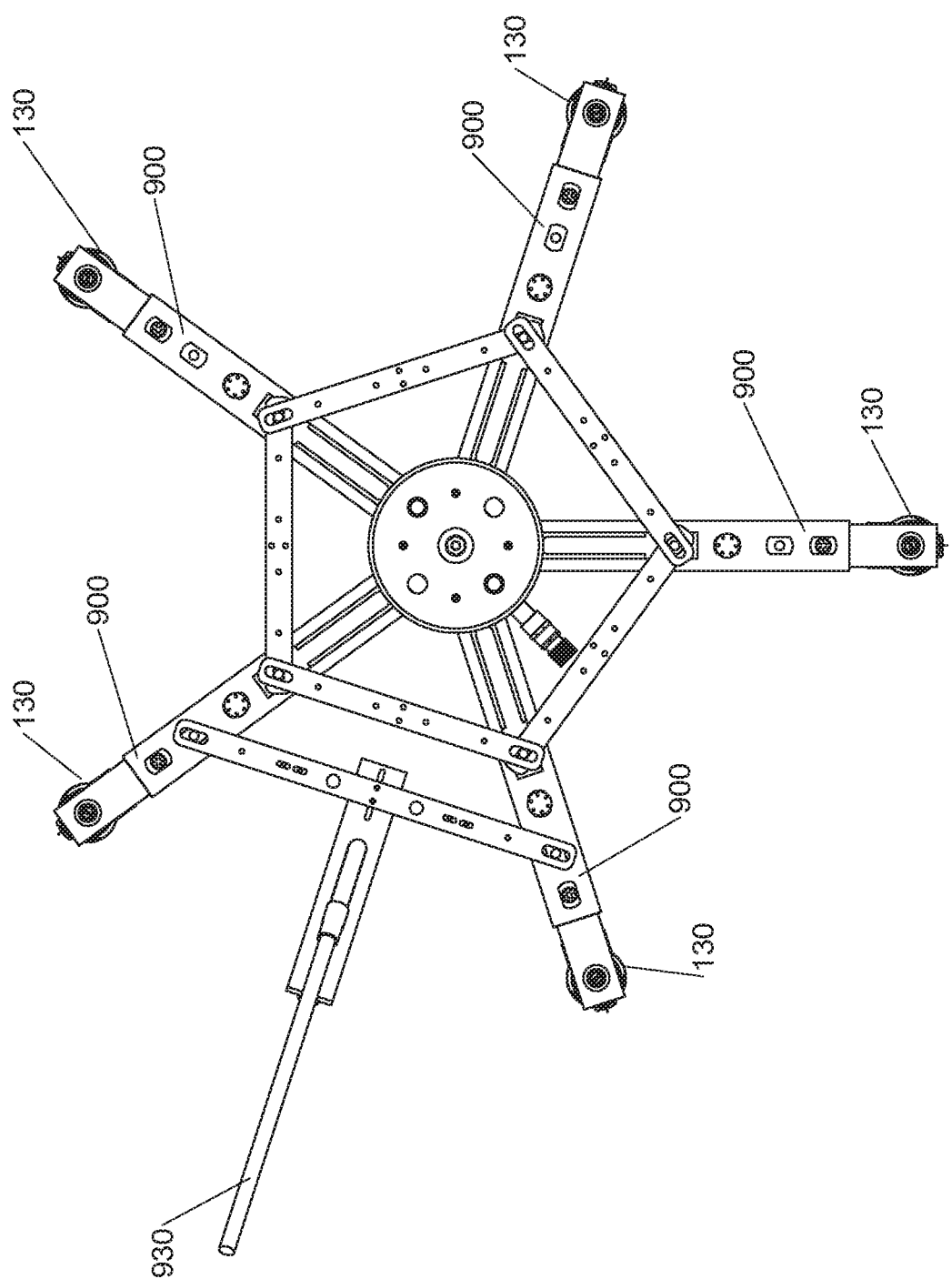
FIG. 22 depicts a top view of the legs and leg support structure of an embodiment of the invention.

Referring now to FIG. 22, a top view of an embodiment of a leg assembly of the invention, showing five legs 900 and optional casters on each leg, and showing exemplary supporting structure for same, is depicted. Pull handle 930 may be attached to the leg assembly, and is useful for comfortably pulling or pushing a kiosk of the invention in a rolling engagement on support surface 002 (not shown in FIG. 22) into a desired location.

Figure 23:
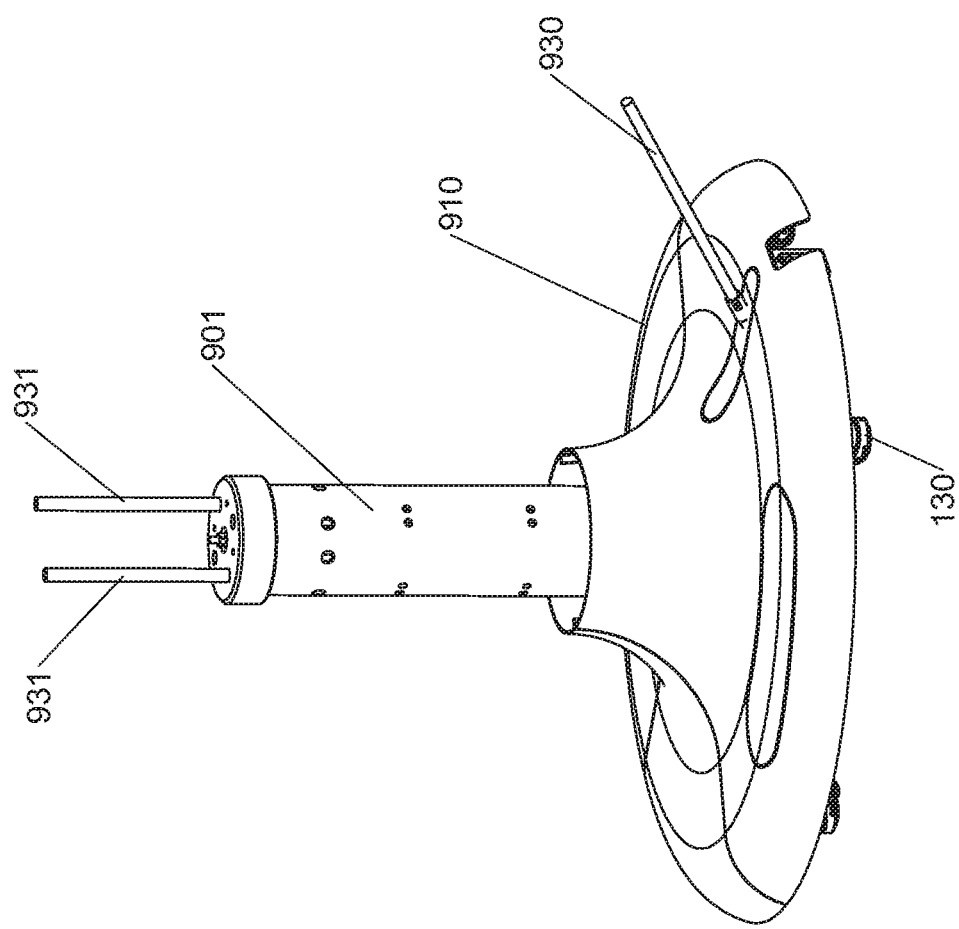
FIG. 23 depicts a perspective view of the leg cover, one of tubes of the vertical lift assembly, and cable snorkel of an embodiment of the invention.

Referring now to FIG. 23, a perspective view of the leg cover 910, one of tubes of the vertical lift assembly 901, optional casters 130, and cable snorkels 931 of an embodiment of the invention are depicted.

Figure 24:
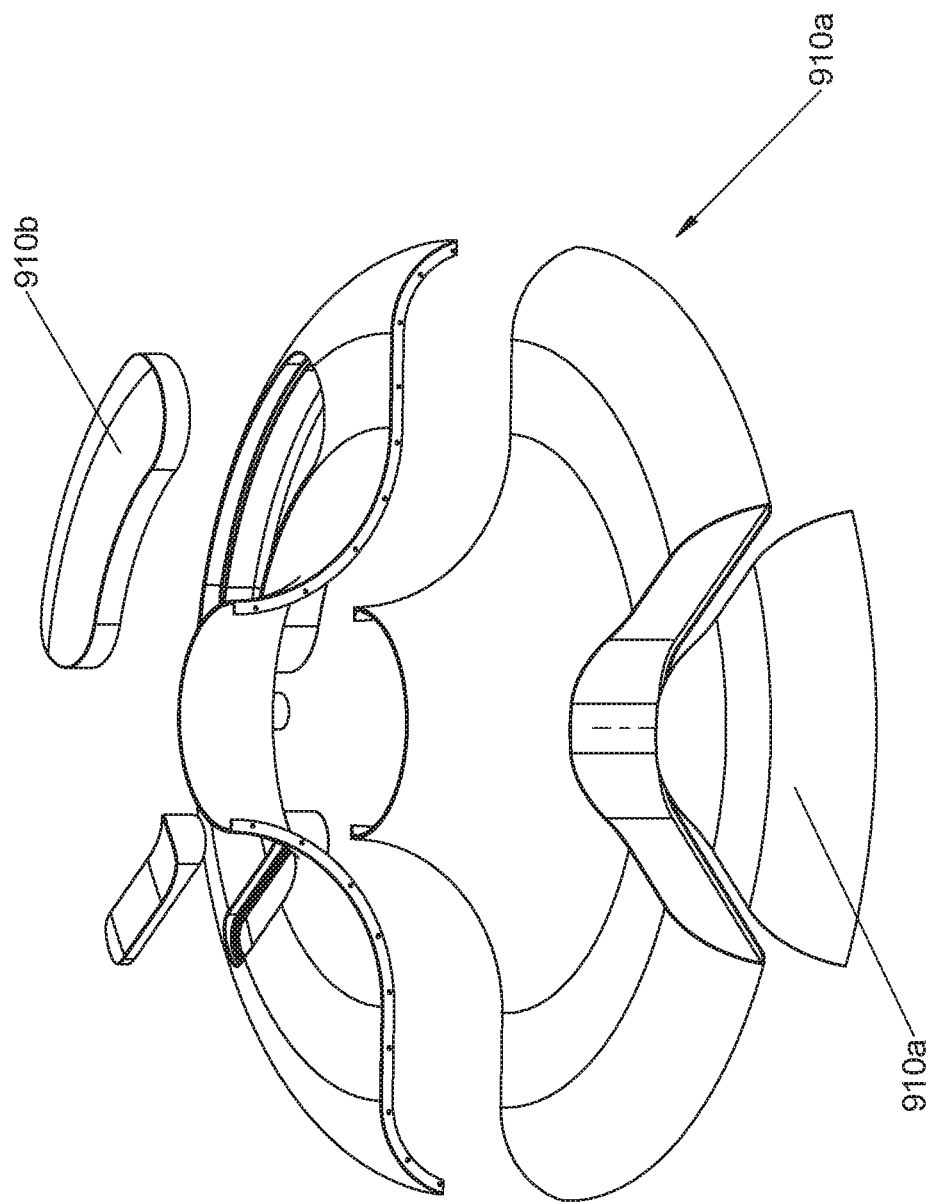
FIG. 24 depicts a perspective view of an embodiment of the leg cover of the invention, showing the recess to accommodate a wheelchair, scooter or other mobility device of a patient undergoing eye examination at the eye examination kiosk.

Referring now to FIG. 24, a perspective view of an embodiment of the leg cover 910 of the invention, showing a recess cover 910a, that, when removed, accommodates a wheelchair, scooter or other mobility device of a patient undergoing eye examination at the eye examination kiosk is depicted. Also shown is an exemplary utility tray and cover 910b, the tray being for storage of tools or other useful articles.

Figure 25A:
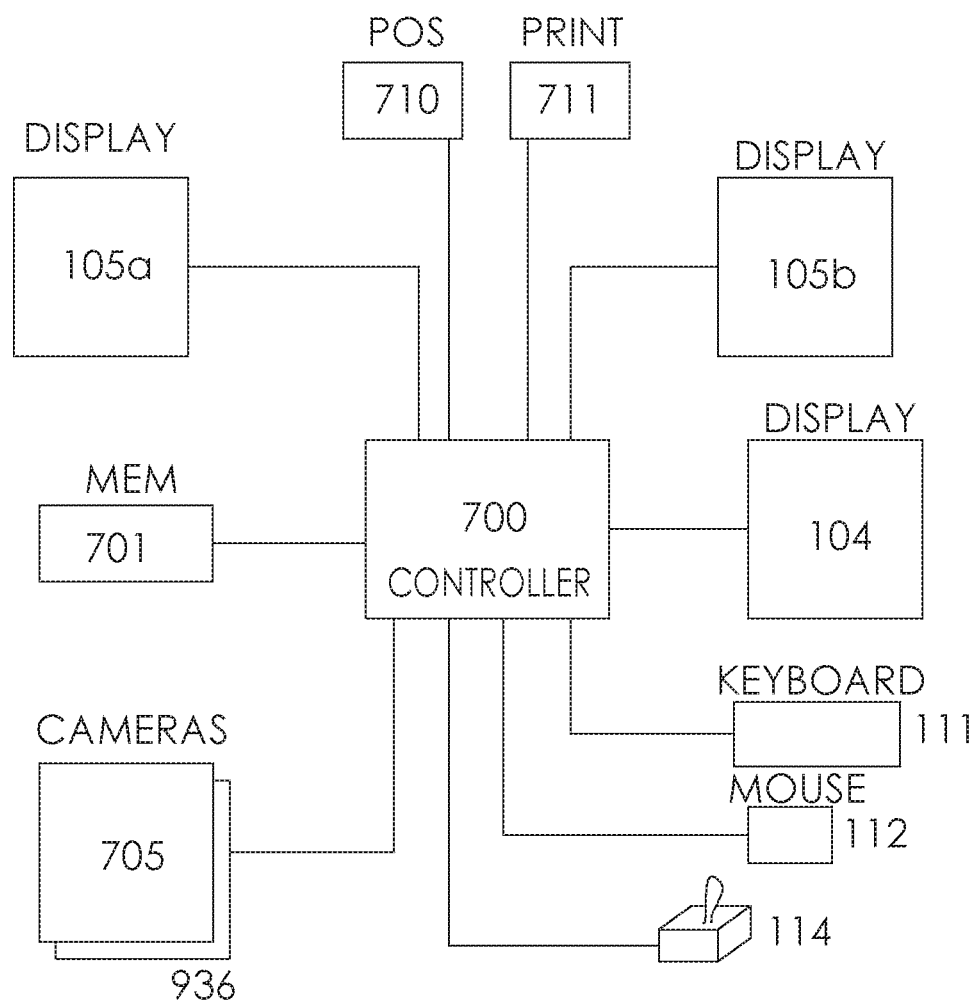
FIG. 25A depicts a partial block diagram of an embodiment of the eye examination kiosk of the invention, depicting the displays, computer readable media, camera, keyboard, mouse, joystick, point-of-sale system and thermal printer in communication with the controller of the invention.

Referring now to FIG. 25A, a partial block diagram of the eye examination kiosk of the invention, depicting displays 105a and 105b, computer readable media 701, security camera 705, keyboard 111, mouse 112, joystick 114, point-of-sale system 710 and thermal printer 711 in communication with controller 700, is depicted. Controller 700 may be in communication with computer readable media 701, which may be a computer memory device or plurality of devices, which comprises non-transitory computer readable and executable instructions which, when read and executed by controller 700, perform the steps and functions of the invention, either autonomously or on command from an operator through voice, touch screen or directly typed commands, or by way of wired or wireless communication from a remote computing devices which may be, for example, any remote computer, a tablet, smart phone or other device that is in communication with controller 700. Controller 700 is also in communication with displays 105a and 105b which may be used, for example, to display advertising and other messaging so as to be visible to persons who are in proximity to the eye examination kiosk of the invention. Controller 700 may also be in communication with optional point of sale terminal 710 and printer 711 which may be used to receive payment from patients or other persons and to print receipts. Such payments may be transacted, for example, by a patient's use of a credit card or debit card, or other similar readable device, capable of transmitting payment authorization as may be required to pay for services provided by the eye examination kiosk of the invention. Controller 700 may also be in communication with display 104 which may be, for example, a flat screen display of any type or maybe a touch screen capable of receiving input from a user. Display 140 may also be utilized for displaying any information, video, or other images to a viewer or other person, including kiosk status and patient information and examination results. Controller 700 may also be in communication with keyboard 111, mouse 112, and/or joystick 114 all of which may be used by a patient, kiosk operator, or other person to enter commands to control the steps and functions of the eye examination kiosk and method of the invention. Controller 700 may also be in communication with a camera 705 which may be disposed inside the kiosk outer shell or made be disposed on outer surface of the kiosk outer shell or other surface so as to provide video information to a remote viewer through the kiosk network connection, or maybe used to capture video which is recorded in computer readable media 701 or other storage media as may be known in the art. Controller 700 may also be in communication with a camera 936 which may be utilized to capture images of a patient.

Figure 25B:
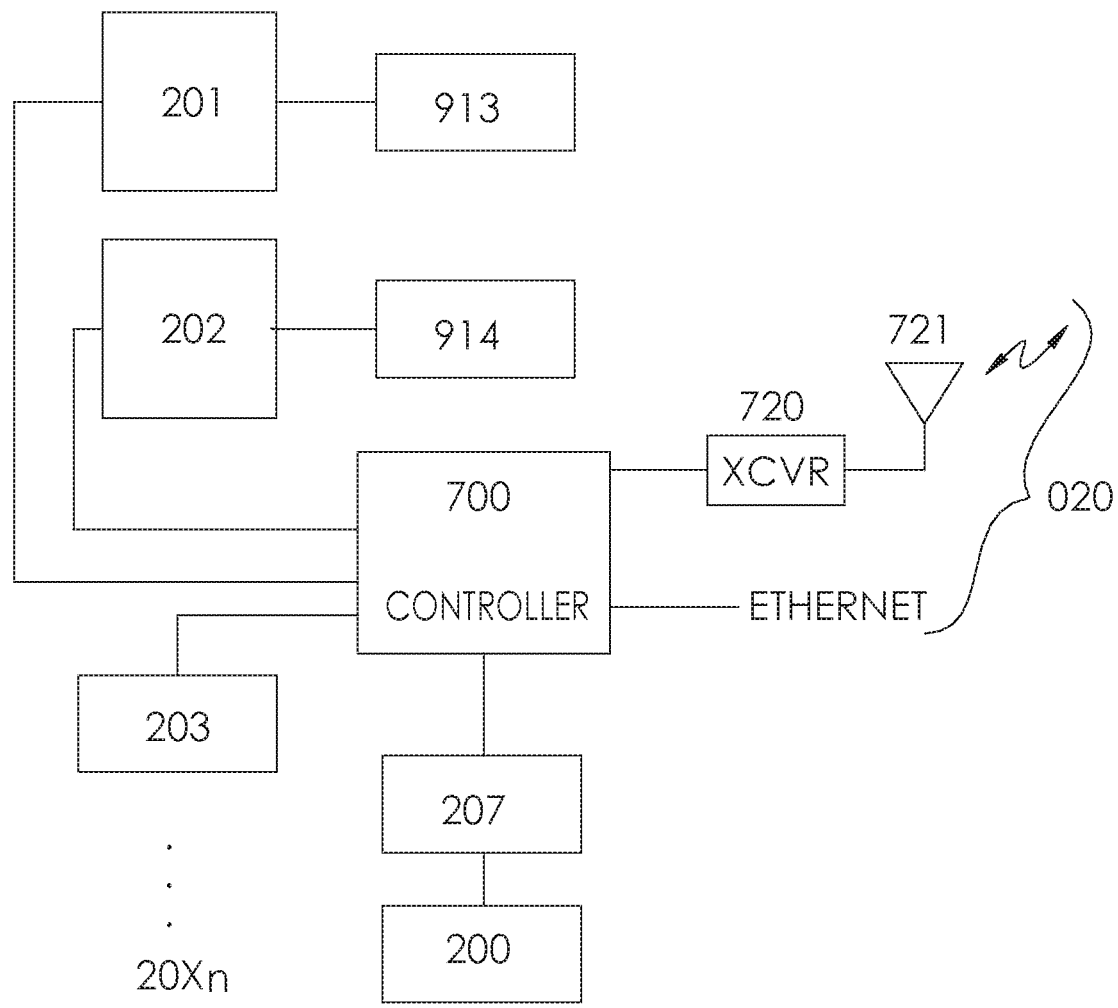
FIG. 25B depicts a partial block diagram of an embodiment of the eye examination kiosk of the invention, depicting eye examination devices, cameras, wireless transceiver and Ethernet connections in communication with the controller of the invention.

Referring now to FIG. 25B, a partial block diagram of the eye examination kiosk of the invention, depicting eye examination devices 201 and 202, wireless transceiver 720 and antenna 721 and Ethernet or other wired data connections in communication with controller 700, is depicted. Controller 700 is in communication with eye examination devices such as, for example, 201, 202, and 200. Eye examination devices 201 and 202 may comprise visual displays 913 and 914 which may be touch screens and may be intended to provide information to an operator and to allow control of the devices. Controller 700 may also be in communication with wireless transceiver 720 which may in turn be in communication with antenna 721, enabling wireless RF communication between controller 700 and a data network as further depicted in FIG. 13. In this manner, the eye examination kiosk of the invention may be in wireless data communication with the Internet or World Wide Web as further described below. Controller 700 by also be in wired communication with an exterior data network via an Ethernet or other wired data connection. Thus controller 700 may be in communication with the Internet, World Wide Web, or other data network via a wired connection.

Figure 25C:
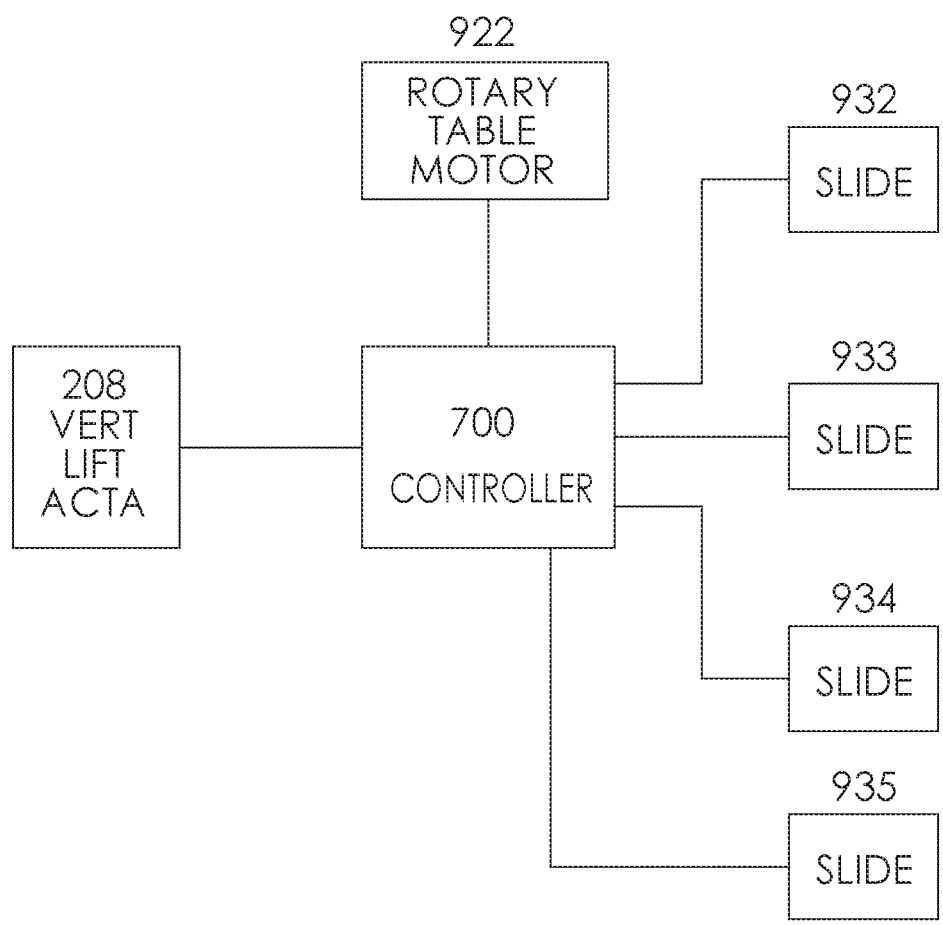
FIG. 25C depicts a partial block diagram of an embodiment of the eye examination kiosk of the invention depicting the three axis positioning and rotating system elements of the invention and communication with the controller.

Referring now to FIG. 25C, a partial block diagram of the eye examination kiosk of the invention depicting the three axis positioning and rotating system elements of the invention and communication with controller 700, is depicted. Controller 700 is in communication with controllable rotary table motor 922; eye examination device and controllable camera actuators/slides 932, 933, 934 and 935; and controllable vertical actuator 905 forming a multi-axis positioning system with rotation.

Figure 26:
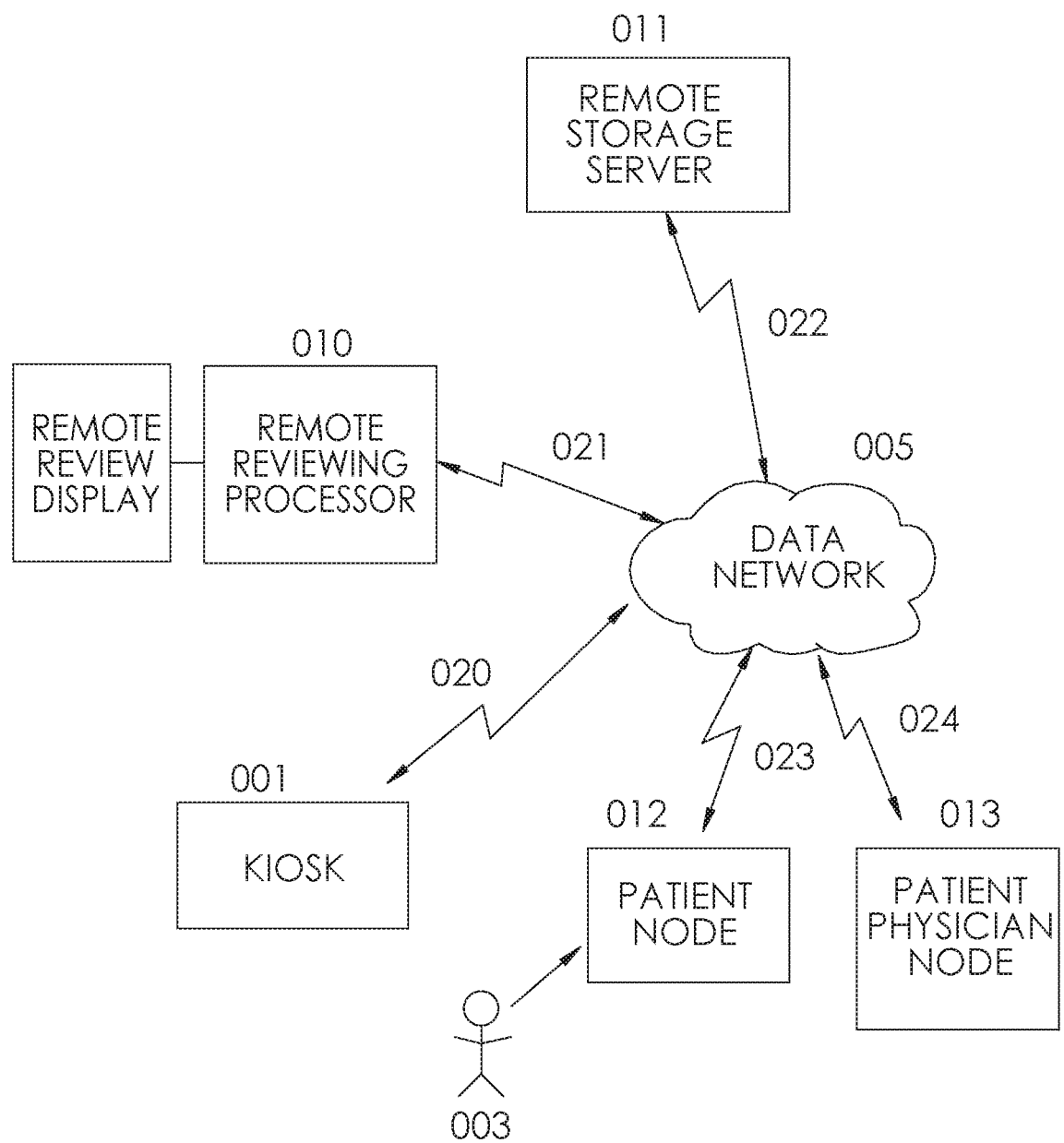
FIG. 26 is a block diagram depicting the eye examination kiosk of the invention connected to a remote storage server computer via a network connection, which may be wired or wireless, and which may be the internet or world wide web. Also depicted is a remote eye examination report reviewing computer, or server, which may be utilized by a physician for remote reading of eye examination results. The remote eye examination report reviewing computer is connected to the remote storage server, patient, patient's physician, and kiosk via a data network which may be, for example, the Internet.

Referring now to FIG. 26, a block diagram depicting eye examination kiosk 001 connected to remote storage server computer 011 via network connection 020, which may be wired or wireless, and which may be any network including but not limited to the Internet or World Wide Web, is depicted. Also depicted is remote eye examination report reviewing computer 010 and display 010*a* which may be utilized by a physician for remote reading of eye examination results or reports. Remote eye examination report reviewing computer 010 is connected to remote storage server 011, patient, patient's physician, and kiosk 001 via data network 005 which may be, for example, the world wide web or Internet. Remote eye examination report reviewing computer 010 is in communication with data network 005 via data connection 021. Likewise, patient node 012 which may be an electronic device capable of communicating via a data network such as a smart phone, computer, tablet, or any other electronic device, may be in communication with data network 005 through data connection 023 such that a remote reviewing physician utilizing a remote reviewer server 010 may communicate eye examination results, diagnoses, and suggestions for follow-up treatment to patient 003. Still further, a remote reviewing physician may transmit this information to predesignated patient physician node 013, which may be for example, a computer, tablet or other electronic device, such that the patient's physician or other patient-designated person or entity may also receive eye examination results, suggestions for follow-up treatment, or the like. Patient physician node 013 is in communication with data network 005 via data connection 024. Patient eye examination results, remote physician results, diagnoses, suggestions for follow-up treatment, payment information and any other information related to the eye examination of a patient may be stored in remote storage server 011 which is in communication with data network 005 by connection 022. This information may be retrieved by any user of the system who has authorization through data network 005 and connection 022. Any of the data network connections 020, 021, 022, 023, or 024 may be wired or wireless, serial or parallel, or any other data connection type known in the art. Data network 005 may be any data network, including but not limited to the Internet or World Wide Web.

Figure 27:
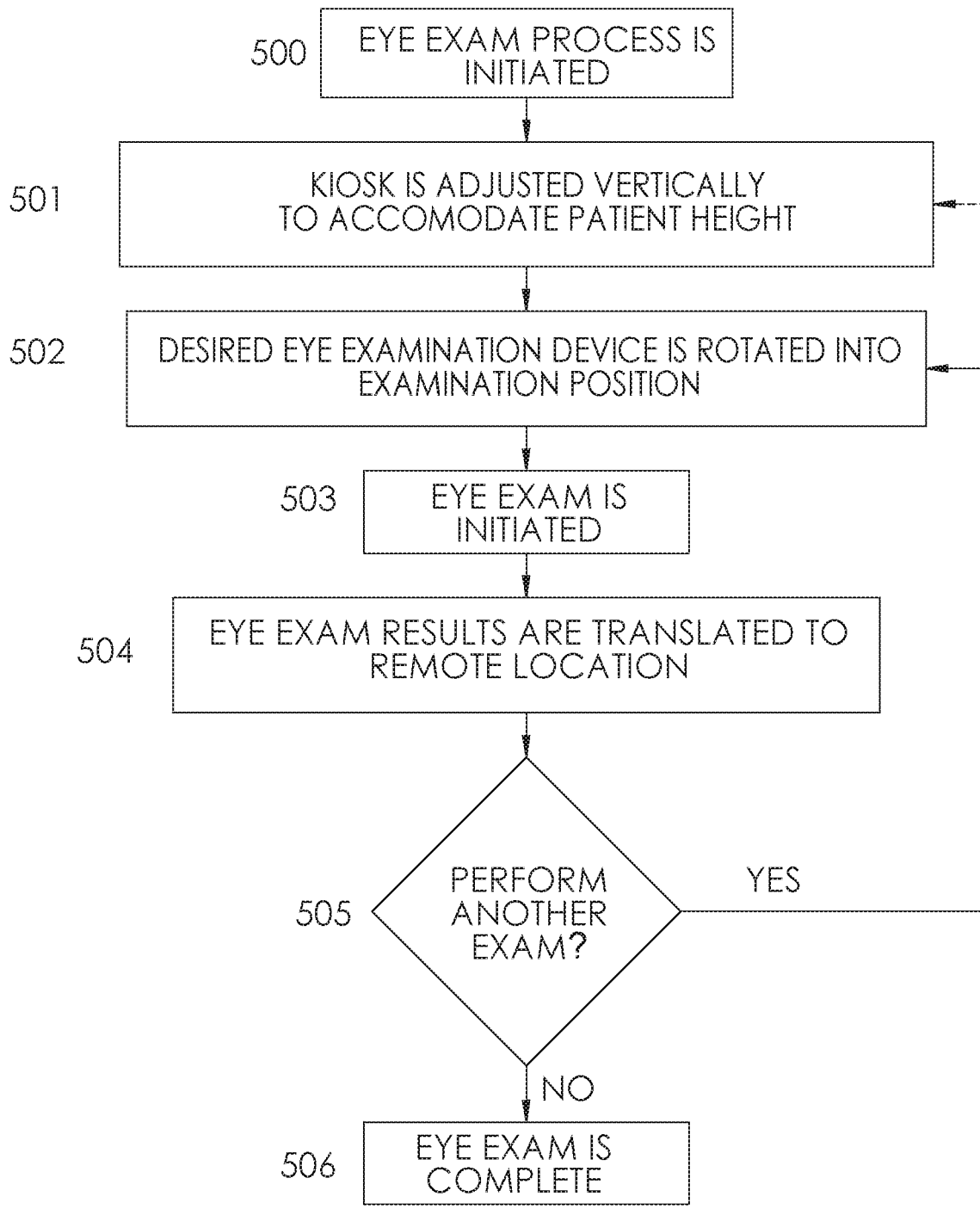
FIG. 27 depicts a flow diagram of the eye examination steps of an embodiment of the invention.

Referring now to FIG. 27, a flow diagram of an embodiment of the eye examination steps of the invention is depicted. Elements of FIGS. 1-13 are also referred to in describing the eye examination steps. In first step 500, the eye examination process is initiated. This may occur by a patient approaching the eye examination kiosk of the invention and providing patient identification information, past medical history, current symptoms or other medical information, and making payment using, for example, point-of-sale system 710. The inputting of this information may be automated by sequential display of prompts on display 104, or may be assisted by a kiosk operator. The information may be inputted to controller 700 by the patients or operators use of keyboard 111, mouse 112, joystick 114, or in the case in which display 104 is a touchscreen, by utilizing the touchscreen features of display 104. The patient may also input to controller 700 the identification of the patient's current medical providers, if any. The information thus provided by the patient may be transmitted to remote storage server 011 via data connection 020, data networks 005 and data connection 022. In the second step 501, the kiosk height may be adjusted by the vertical lift actuator assembly so that the kiosk eye examination devices are aligned with the patient's eyes, so that eye examination of the patient may occur. In the third step 502, a kiosk operator may determine which eye examination device is desired to be used for an eye examination of patient 003 and may command controller 700 to rotate rotable table 108 and to translate rotable table 108 using the three axis positioning system of the invention such that the desired eye examination device is disposed so that its plane of examination is aligned with the patient's eye or eyes, allowing eye examination to begin. In the fourth step 503, the kiosk operator may command controller 700 to issue an initiate command to the eye examination device such that an eye examination is initiated. In the fifth step 504, after the eye examination has concluded, the eye examination results may be transmitted to remote storage server 011 for later retrieval and review by a remote physician operating remote reviewer server 010. In a sixth step 505, a determination is made as to whether further eye examination is required. If no further eye examination is required, the eye examination procedure is terminated, and the patient may wait to be contacted by the remote reviewing physician, or by the patient's own physician who was previously identified during the initial step in which the patient provided this information. If further eye examination is required, steps 501 through 504, or steps 502 through 504, are repeated until all eye examinations have been completed.

In an embodiment, a camera such as 936 in communication with controller 700 may be utilized to provide images of a patient for purposes of determining the proper height to which the eye examination devices must be translated in order for proper alignment with the patient's eye may be realized. Controller 700 may execute non transitory computer readable instructions for the steps of 1) determining whether the patient's eyes are below or above an examination axis of the eye examination device; 2) estimating the amount of travel required to translate the eye examination device to be property aligned with the patient's eyes; 3) translating the eye examination device up or down by the amount of estimated travel required to cause the eye examination device to be property aligned with the patient's eyes 4) capturing a new camera still or video image to determine whether the patient's eyes are below or above an examination axis of the eye examination device; and 5) repeating steps 2, 3 and 4 until the eye examination device is property vertically aligned with the patient's eye or eyes such that eye examination can take place.

Figure 28:
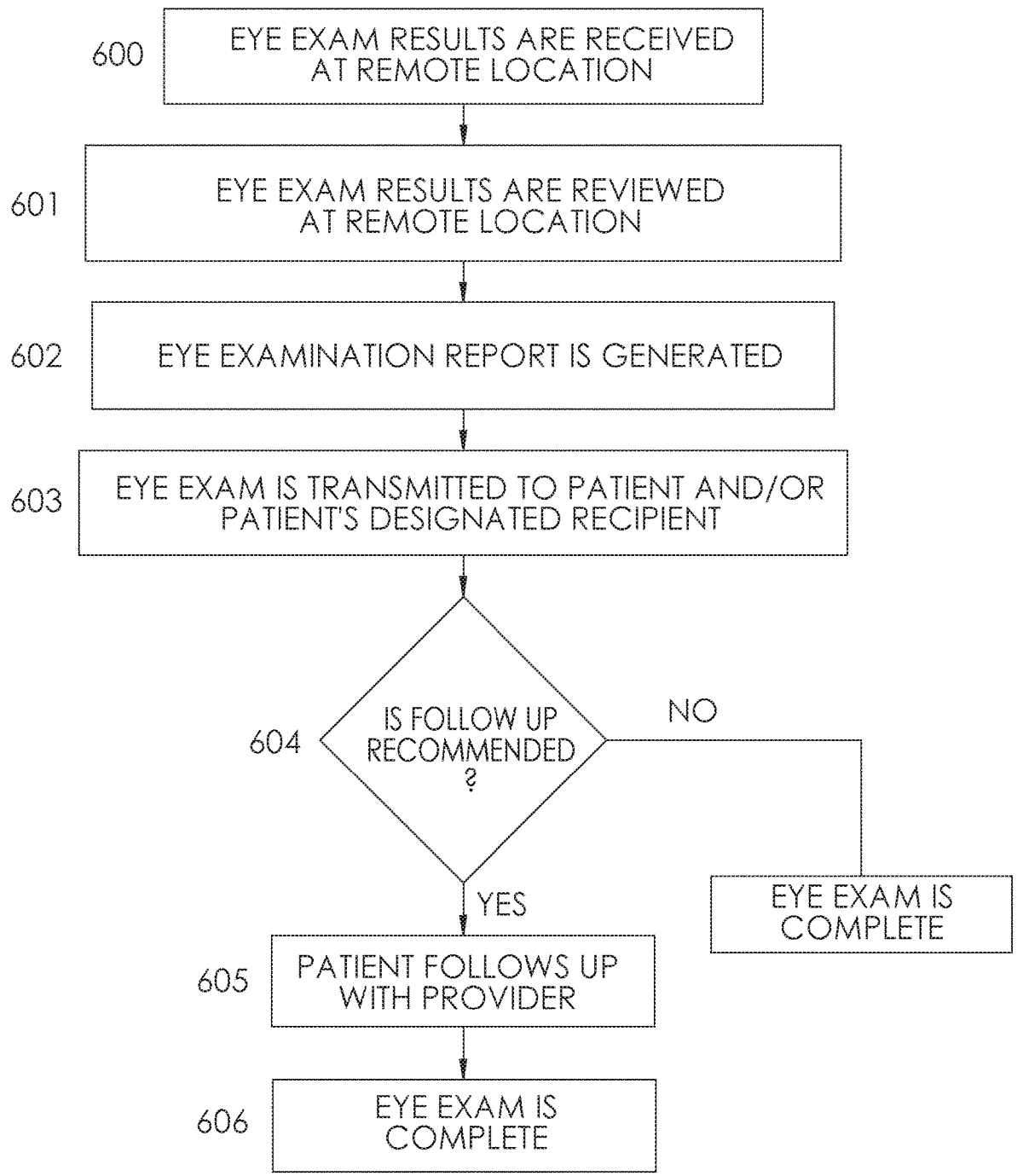
FIG. 28 depicts a flow diagram of the remote reading of eye examination results according to an embodiment of the invention.

Referring now to FIG. 28, a flow diagram of an embodiment of the remote reading of eye examination results is depicted. Once an eye examination has taken place as described relative to FIG. 14, the eye examination results are transmitted to remote storage server 011 via connections 020, 022 and data network 005 which may be, for example, the Internet. Thus, in the first step 600, the eye examination results are received and stored at remote storage server 011. A remote physician may utilize remote reviewer server 010, data connection 021, data networks 005, and data connection 022 to retrieve the eye examination results for particular patient 003. Once the eye examination results have been retrieved they may be reviewed in step 601 by the remote physician. The remote physician may then generate information useful to the patient and to the patient's physician such as an eye examination report with findings, suggestions for follow-up, and identification of appropriate physicians in the local community in which the patient resides if, for example, the patient has not indicated that they currently have a physician. This information may be transmitted in step 603 to the patient and/or the patient's designated recipient who may be any person, but is preferably the patient's physician. If the eye examination report recommends follow-up treatment step 604, the patient follows up either with a suggested medical provider or with their own physician as appropriate.

Figure 29:
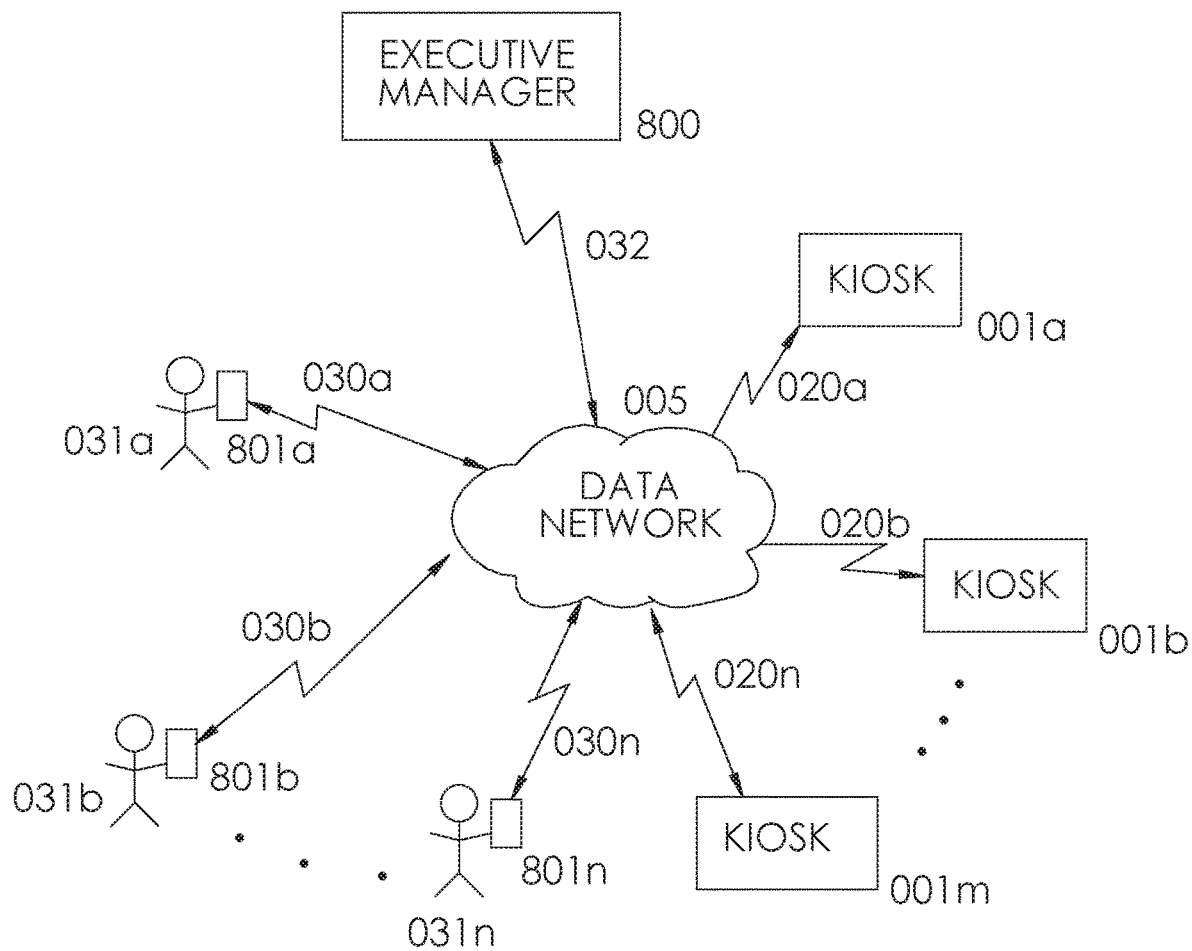
FIG. 29 is a block diagram depicting an embodiment of the invention in which the eye examination results are made available to one or more, but preferably a plurality, of physicians, and wherein one of the physicians may select a particular eye examination result for reviewing. The reviewing physician may be located geographically remote from the kiosk.

Referring now to FIG. 29, a description of one embodiment of the invention in which the eye examination results are made available to a plurality of physicians 031a, 031b, through 031n, where "n" can be any number of physicians, and wherein one of the plurality of physicians may select a particular eye examination results for reading, is depicted. In this embodiment of the invention, the remote reading, analysis, interpretation of eye examination results, and the generation of suggestions for follow up treatment or care may be performed by any one of a plurality of physicians 031a-031n, each of whom may log into the system remotely for the purpose of reading eye examination results by communicating with executive manager 800 over one of network connections 030a through 030n, data network 005, and network connection 032. Executive manager 800 may keep a first list comprising a current listing of eye examination results that have not been read or reviewed by a physician ("unread examination results"). Executive manager 800 is in communication with data network 005 via network connection 032, and data network 005 may in turn be in communication with a plurality of eye examination kiosks 001a, 001b through 001m, where "m" can be any number. Executive manager 800 may also have a second list comprising a listing of the identities of physicians who are available to read eye examination results ("currently available physicians"). Any physician 031i who wishes to have his/her name included in the list of currently available physicians may notify executive manager 800 that he/she is available by transmitting a signal containing a first predetermined data field to executive manager 800. Likewise, any physician 031i who is listed by executive manager 800 as being a currently available physician may make himself or herself unavailable by transmitting a signal containing a second predetermined data field to executive manager 800. Each currently available physician may log into a communication portal, which may for example be a password protected internet-connected web site, and which is in communication with executive manager 800. In an embodiment, the logging in of a physician into the communication portal may be an event that causes executive manager 800 to designate that physician as a currently available physician, and the logging out of a currently available physician may be an event that causes executive manager 800 to designate that physician as currently unavailable. Any of data network connections 020a-020n, 032, or 030a-030n may be wired or wireless, serial or parallel, or any other data connection type known in the art.

Still referring to FIG. 29, once a currently available physician has logged into the communication portal, executive manager 800 may cause the current listing of unread examination results to be transmitted to a currently available physician's electronic device 801a, 801b through 801n whereupon the current listing of unread examination results may be displayed upon the display of the electronic device 801i for review by the currently available physician 031i. The currently available physician 031i may then select an unread examination result for reading, analysis, and generation of recommendations for follow up treatment. Once selected, the unread examination is removed from the unread examination list. The unread examination list presented to a currently available physician may be organized and presented in any order, such as, for example, "first in-first out" or any other order as may be desired. Upon selection of an unread examination result for reading, analysis, and generation of recommendations for follow up treatment, the physician's electronic device 801i may transmit a message to executive manager 800, causing the unread examination result to be transmitted to the electronic device 081i of the physician and to be displayed upon the electronic display of electronic device 081i. The currently available physician 031i may then read the downloaded eye examination results, generate a report, and transmit the report to executive manager 800. Executive manager 800 may then cause the report to be transmitted to the patient and to any person or entity the patient has designated, including but not limited to the patient's personal physician. The system of the invention may comprise any number of currently available physicians 031i, and it may comprise any number of kiosks 001i. Because the currently available physicians and the kiosks are in communication with executive manager 800 through network connections 030a-030n and 020a-020n, and data network 005, the currently available physicians 031i and the kiosks 001i may be geographically located anywhere, and thus need not be co-located, as long as communication with data network 005 is maintained.

In still a further embodiment of the invention, eye examinations in which photographs or other images of the eye are taken using the above described apparatus or method, and the analyses of the images may be performed automatically by the system of the invention. Such automatic analyses may be carried out by a controller in communication with the system of the invention, in which the controller executes non-transitory computer executable instructions for identifying pre-defined image features that may indicate medical or other conditions of which the patient should be made aware, which indicate the likelihood of certain diseases in the patient, or which may indicate further follow up medical care and treatment by a physician. The non-transitory computer executable instructions may be stored in a computer readable media that is in communication with the controller. The controller may be any controller that is in communication with remote storage server 011 (FIG. 26) or is in direct communication with the examination devices, and may therefore be geographically located anywhere, including remotely located from the examination devices, or co-located with the examination devices in, on, or near the kiosk. The results of the automatic image analyses performed by the controller may be transmitted to a physician for inclusion in the reviewing physician's report, or may be transmitted directly to the patient or to the patient's personal physician. Using this automatic reading function, certain eye examinations may be carried out immediately upon completion of the kiosk eye examination, and may be transmitted to the patient within a short time of the examination. It can be seen that this embodiment of the invention may eliminate the need for a remote server and reading center altogether, and will eliminate the need for any reading physician in order for the reading and analyses of the images and other examination information recorded by the eye examination device. In this embodiment of the invention, the eye examination, reading, analysis and referral steps of the invention are carried out with any human action required.

INDUSTRIAL APPLICABILITY

The eye examination kiosk and method provides a useful and novel system and method for providing ophthalmologic telemedicine health care services to individuals. Using the system and method of the invention, a user may have may have ophthalmologic diagnostic images taken at virtually any geographic location and may receive a reading of the examination and recommendations for referral to a treating physician by electronic means such as email, text messaging or otherwise. The system and method of the invention comprise a structure for rotating and/or translating ophthalmologic examination devices such as an auto-refractor, an auto-keratometer, a corneal topographer, a fundus camera, an external photo camera, a perimeter, a lensmeter, a specular microscope, a retinal and external eye imager, an Optical Coherence Tomographer (OCT), or a non-contact tonometer into a position such that they may be used for examination of a patient. The kiosk outer shell may comprise an opening allowing the ophthalmologic examination equipment to perform eye examinations of a patient. Eye examination results are transmitted to a remote location where they are read by a physician, who transmits examination findings and recommendations for follow up treatment to the patient. The results may include the identity of qualified physicians who practice geographically near the patient, or who are qualified to treat a patient for a specific condition indication.

What is claimed is:

1. An eye examination kiosk, comprising:
   a controllable rotable table rotable about an axis, said rotable table in communication with a controller and controllable to be indexed to predefined points of rotation;
   at least one eye examination device, wherein said at least one eye examination device is mounted to a surface of said rotable table;
   a kiosk outer shell;
   a vertical lift assembly controllable by said controller to extend or retract vertically;
   wherein said kiosk outer shell is attached to said vertical lift assembly either directly or indirectly;
   wherein said rotable table is rotable upon command from said controller such that said at least one eye examination device can be within said outer kiosk shell rotated into a predefined point of rotation such that said at least one eye examination device presented to a patient for eye examination of the patient;
   wherein an attachment between at least one of said at least one eye examination devices and said rotary table further comprises a controllable eye examination device actuator and slide assembly in communication with said controller disposed between said eye examination device and said rotary table, said controllable eye examination device actuator and slide assembly being extendable and retractable upon command by said controller, such that said at least one of at least one eye examination device is translatable horizontally towards or away from an eye of a user by command to said controllable eye examination device actuator from said controller;
   wherein said at least one eye examination device is capable of producing eye examination results and communicating said eye examination results to said controller, and wherein said controller is in communication with a remote storage server computer via a data network for transmitting said eye examination results to said remote storage server computer;
   wherein said kiosk outer shell encloses said rotable table and said at least one eye examination device, and wherein said kiosk outer shell comprises an examination opening at said predefined point of rotation, said opening allowing said patient's head to be disposed such that the patient may be examined by said at least one eye examination device without physical interference between said patient's head and said kiosk outer shell;
   wherein said kiosk outer shell is attached to said vertical lift assembly such it is translated vertically up or down by said vertical lift assembly when said vertical lift assembly is commanded to extend or retract vertically, respectively, by said controller so as to accommodate patients at differing heights measured from a ground level to the patient's line of sight, while allowing said controllable rotable table to be rotated within said kiosk outer shell when said kiosk outer shell has been translated vertically; and
   wherein said rotary table and said at least one eye examination device are enclosed by said kiosk outer shell whether the eye examination kiosk is in either a raised or lowered position.

2. The eye examination kiosk of claim 1, wherein said at least one eye examination device is further defined as being selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer, and a non-contact tonometer.

3. The eye examination kiosk of claim 2, wherein said autorefractor and said autokeratometer are housed with a single housing.

4. The eye examination kiosk of claim 1, wherein said vertical lift assembly is further defined as comprising an first tube having a first axis, said first tube slidingly engaged with a second tube having a second axis, wherein said first axis and said second axis are coaxial and wherein said sliding engagement between said first tube and said second tube allows said first tube and said second tube to slide along one another along said first and second axes, one tube within the other; and wherein said vertical lift assembly further comprises a controllable vertical lift actuator having a first end and a second end, said first end attached to said first tube and said second end attached to said second tube, said actuator disposed such that when it extends, said second tube is translated on said sliding engagement along said first tube in a first axial direction along said axis, and when said actuator retracts, said second tube is translated on said sliding engagement along said first tube in a second axial direction along said axis; and wherein said first tube is attached to a plurality of legs for supporting said vertical lift assembly on a support surface;

such that when said controllable vertical lift actuator is extended upon command, said rotary table and said outer shell are translated in an upward direction, away from said support surface, and when said controllable vertical lift actuator is retracted, said rotary table and said kiosk outer shell are translated in an downward direction, towards said support surface;

wherein said controllable actuator is in communication with said controller for commanding the extension and retraction of said controllable vertical lift actuator.

5. The eye examination kiosk of claim 1, wherein said kiosk comprises a plurality of eye examination devices, and where the attachment between each of said eye examination devices and said rotary table further comprises a controllable eye examination device actuator and slide assembly in communication with said controller disposed between said eye examination device and said controllable rotary table, said controllable eye examination device actuator and slide assembly being extendable and retractable upon command by said controller, such that each of said plurality of eye examination devices is translatable towards or away from said outer shell by command to said controllable eye examination device actuator from said controller.

6. The eye examination kiosk of claim 5, further comprising a point of sale system in communication with said controller.

7. The eye examination kiosk of claim 1, wherein said controllable rotable table comprises a male V-groove, and wherein said controllable rotable table is supported by a plurality of rotable thrust bearings each comprising a complimentary V-groove such that when said rotable table male V-groove is engaged with said rotable thrust bearing V-grooves, said controllable rotable table is supported by said rotable thrust bearings while said controllable rotable table is allowed to rotate about an axis, and wherein said plurality of rotable thrust bearings are attached to a surface of said support plate, and wherein a rotary gear ring is attached to a surface of said controllable rotable table, said rotary gear ring having a arcuate pattern of teeth in a toothed engagement with a rotary drive gear driven by a controllable rotary drive motor in communication with said controller such that when said controller commands said rotary drive motor to rotate about an axis, said rotary drive gear drives said rotary gear ring causing said controllable rotable table to rotate about an axis.

8. The eye examination kiosk of claim 4, wherein said controllable rotable table comprises a male V-groove, and wherein said controllable rotable table is supported by a plurality of rotable thrust bearings each comprising a complimentary V-groove such that when said controllable rotable table male V-groove is engaged with said rotable thrust bearing V-grooves, said rotable table is supported by said rotable thrust bearings while said controllable rotable table is allowed to rotate about an axis, and wherein said plurality of rotable thrust bearings are attached to a surface of said support plate, and wherein a rotary gear ring is attached to a surface of said controllable rotable table, said rotary gear ring having a arcuate pattern of teeth in a toothed engagement with a rotary drive gear driven by a controllable rotary drive motor in communication with said controller such that when said controller commands said rotary drive motor to rotate about an axis, said rotary drive gear drives said rotary gear ring causing said controllable rotable table to rotate about an axis.

9. The eye examination kiosk of claim 5, wherein said controllable rotable table comprises a male V-groove, and wherein said controllable rotable table is supported by a plurality of rotable thrust bearings each comprising a complimentary V-groove such that when said controllable rotable table male V-groove is engaged with said rotable thrust bearing V-grooves, said controllable rotable table is supported by said rotable thrust bearings while said rotable table is allowed to rotate about an axis, and wherein said plurality of rotable thrust bearings are attached to a surface of support plate, and wherein a rotary gear ring is attached to a surface of said controllable rotable table, said rotary gear ring having a arcuate pattern of teeth in a toothed engagement with a rotary drive gear driven by a controllable rotary drive motor in communication with said controller such that when said controller commands said rotary drive motor to rotate about an axis, said rotary drive gear drives said rotary gear ring causing said controllable rotable table to rotate about an axis.

10. A method for eye examination, comprising the steps of:

a. providing an eye examination kiosk comprising:

a plurality of eye examination devices mounted onto a controllable rotable table, each eye examination device of said plurality of eye examination devices having a predefined axis of examination said controllable rotary table adapted to be commanded to rotate upon command from a controller, said controller in communication with non-transitory physical computer readable media containing computer readable instructions for rotating said controllable rotable table to predefined points of rotation, one for each eye of said plurality of examination devices, such that each of said plurality of eye examination devices is presented to a patient for eye examination of the patient, said eye examination kiosk further comprising an attachment between at least one of said plurality of eye examination devices and said controllable rotable table, said attachment further comprising a controllable eye examination device actuator and slide assembly in communication with said controller disposed between each of said plurality of eye examination devices and said controllable rotable table, said controllable eye examination device actuator and slide assembly being extendable and retractable upon command by said controller, such that said at least one of said plurality of eye examination devices is translatable horizontally towards or away from an eye of a user by command to said controllable eye examination device actuator from said controller, said eye examination kiosk further comprising a kiosk outer shell enclosing said controllable rotable table and plurality of eye examination devices such that said controllable rotable table and plurality of eye examination devices rotate within said kiosk outer shell; a vertical lift assembly controllable by said controller to translate said eye examination kiosk vertically either upwards or downwards when commanded by said controller so as to accommodate patients at differing heights measured from a ground level to the patient's line of sight, while allowing said controllable rotable table to be rotated within said kiosk outer shell when said kiosk outer shell has been translated vertically, wherein the kiosk outer shell is attached to the vertical lift assembly either directly or indirectly;
b. commanding said eye examination kiosk into translate vertically so as to accommodate patients at differing heights measured from a ground level to the patient's line of sight;
c. commanding said controllable rotable table to rotate within said kiosk outer shell into a first predefined point of rotation such that the predefined axis of examination of a first eye examination device of said plurality of said eye examination devices is disposed so as to be in line with a patient's eye, allowing a first examination of said patient's eye;
d. conducting said first eye examination of said patient's eye using said first eye examination device, thereby producing a first eye examination result;
e. commanding said controllable rotable table to rotate into a second predefined point of rotation such that an axis of examination of a second eye examination device of said plurality of said eye examination devices is disposed so as to be in line with said patient's eye, allowing a second examination of said patient's eye;
d. conducting said second eye examination of said patient's eye using said second examination device, thereby producing a second eye examination result;
g. repeating steps d.-e. until said patient's eye has undergone examination by each of said plurality of eye examination devices, thus producing a plurality of eye examination results, one result for each examination;
h. storing each of said plurality of examination results; and
i. transmitting said plurality of eye examination results to a remote computer for retrieval and review by a physician.

11. The method of claim 10, further comprising the steps of:
j. retrieval of said plurality of eye examination results by said physician;
k. review of said plurality eye examination results by said physician;
l. generation of an eye examination report by said physician; and
m. transmitting said eye examination report to said patient.

12. The method of claim 11, wherein the step of generation of said eye examination report by said physician is further defined as including the step of generating recommendations for follow up treatment or diagnostic testing of said patient.

13. The method of claim 11, further comprising the step of transmitting said eye examination report to a third person designated by said patient.

14. The method of claim 12, further comprising the step of transmitting said eye examination report to a third person designated by said patient.

15. The method of claim 10, in which each of the plurality of eye examination devices of said plurality of eye examination devices is selected from the selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

16. The method of claim 11, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

17. The method of claim 12, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

18. The method of claim 13, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

19. The method of claim 14, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

20. A method for eye examination, comprising the steps of:
a. providing an eye examination kiosk comprising:
a plurality of eye examination devices mounted onto a controllable rotable table, each eye examination device of said plurality of eye examination devices having a predefined axis of examination, said controllable rotary table adapted to be commanded to rotate upon command from a controller, said controller in communication with non-transitory physical computer readable media containing computer readable instructions for rotating said controllable rotable table to predefined points of rotation, one for each eye of said plurality of examination devices, such that each of said plurality of eye examination devices is presented to a patient for eye examination of the patient, said eye examination kiosk further comprising an attachment between at least one of said plurality of eye examination devices and said rotary table, said attachment further comprising a controllable eye examination device actuator and slide assembly in communication with said controller disposed between at least one of said plurality of eye examination devices and said controllable rotable table, said controllable eye examination device actuator and slide assembly being extendable and retractable upon command by said controller, such that said at least one of said plurality of eye examination devices is translatable horizontally towards or away from an eye of a user by command to said controllable eye examination device actuator from said controller, said eye examination kiosk further comprising a kiosk outer shell enclosing said controllable rotable table and plurality of eye examination devices such that said controllable rotable table and plurality of eye examination devices rotate within said kiosk outer shell; a vertical lift assembly controllable by said controller to translate said eye examination kiosk vertically either upwards or downwards when commanded by said controller so as to accommodate patients at differing heights measured from a ground level to the patient's line of sight, while allowing said controllable rotable table to be rotated within said kiosk outer shell when said kiosk outer shell has been translated vertically, wherein said kiosk outer shell is attached to said vertical lift assembly either directly or indirectly;

b. commanding said eye examination kiosk into translate vertically so as to accommodate patients at differing heights measured from a ground level to the patient's line of sight;

c. commanding said controllable rotable table to rotate within said kiosk outer shell into a first predefined point of rotation such that the predefined axis of examination of a first eye examination device of said plurality of said eye examination devices is aligned with a patient's eye, allowing a first examination of said patient's eye;

d. conducting said first eye examination of said patient's eye using said first eye examination device, thereby producing a first eye examination result;

e. commanding said controllable rotable table to rotate into a second predefined point of rotation such that an axis of examination of a second eye examination device of said plurality of said eye examination devices is disposed so as to aligned with said patient's eye, allowing a second examination of said patient's eye;

f. conducting said second eye examination of said patient's eye using said second examination device, thereby producing a second eye examination result;

g. repeating steps e.-f. until said patient's eye has undergone examination by each of said plurality of eye examination devices, thus producing a plurality of eye examination results, one result for each examination;

h. storing each of said plurality of examination results;

i. communicating said plurality of eye examination results to a controller for automatic analyses of said plurality of eye examination results, said automatic analyses producing an eye examination report;

j. wherein the step of commanding the rotatory table, for at least one of said plurality of eye examination devices, further comprises the step of translating an eye examination device towards or away from the eye of a user.

21. The method of claim 20, further comprising the steps of:

k. transmitting said eye examination report to said patient.

22. The method of claim 20, wherein the step of generation of said eye examination report by said physician is further defined as including the step of generating recommendations for follow up treatment or diagnostic testing of said patient.

23. The method of claim 21, further comprising the step of transmitting said eye examination report to a third person designated by said patient.

24. The method of claim 22, further comprising the step of transmitting said eye examination report to a third person designated by said patient.

25. The method of claim 20, in which each of the eye examination devices of said plurality of eye examination devices is selected from the selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

26. The method of claim 21, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

27. The method of claim 22, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

28. The method of claim 23, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

29. The method of claim 24, in which each of the eye examination devices of said plurality of eye examination devices is selected from the group consisting of an auto-refractor, an auto-keratometer, a corneal topographer, a fundus camera, an external photo camera, a perimeter, a lensmeter, a specular microscope, a retinal and external eye imager, an Optical Coherence Tomographer (OCT), and a non-contact tonometer.

* * * * *